(12) United States Patent
Smith

(10) Patent No.: US 6,541,610 B1
(45) Date of Patent: Apr. 1, 2003

(54) FUSION PROTEINS COMPRISING TUMOR NECROSIS FACTOR RECEPTOR

(75) Inventor: Craig A. Smith, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 08/406,824

(22) Filed: Mar. 20, 1995

Related U.S. Application Data

(63) Continuation of application No. 08/255,849, filed on Jun. 8, 1994, now abandoned, which is a continuation-in-part of application No. 07/523,635, filed on May 10, 1990, now Pat. No. 5,395,760, which is a continuation-in-part of application No. 07/421,417, filed on Oct. 13, 1989, now abandoned, which is a continuation-in-part of application No. 07/405,370, filed on Sep. 11, 1989, now abandoned, which is a continuation-in-part of application No. 07/403,241, filed on Sep. 5, 1989, now abandoned.

(51) Int. Cl.[7] ............... C07K 14/525; C07H 21/04; C12N 15/19; C12P 21/02

(52) U.S. Cl. .............. 530/387.1; 530/388.1; 435/69.5; 435/69.7; 435/172.3; 435/320.1; 536/23.4; 536/23.52

(58) Field of Search .............. 435/69.5, 69.7, 435/172.3, 320.1; 536/23.4, 23.52; 530/351, 387.1, 388.1

(56) References Cited

U.S. PATENT DOCUMENTS

| | | | |
|---|---|---|---|
| 4,769,326 A | * 9/1988 | Rutter et al. ............... | 435/69.1 |
| 4,935,233 A | 6/1990 | Bell | |
| 4,963,354 A | 10/1990 | Shepard et al. ............ | 424/85.1 |
| 5,073,627 A | 12/1991 | Curtis et al. | |
| 5,075,222 A | 12/1991 | Hannum et al. ........... | 435/69.1 |
| 5,098,702 A | 3/1992 | Zimmerman et al. ..... | 424/85.21 |
| 5,116,964 A | 5/1992 | Capon | |
| 5,118,500 A | 6/1992 | Hänel et al. ............... | 424/85.1 |
| 5,136,021 A | 8/1992 | Dembinski et al. ......... | 530/350 |
| 5,155,027 A | 10/1993 | Sledziewski | |
| 5,258,498 A | 11/1993 | Huston et al. .............. | 530/350 |
| 5,395,760 A | 3/1995 | Smith | |
| 5,477,851 A | 9/1995 | Beutler | |
| 5,478,925 A | * 12/1995 | Wallach et al. ............. | 530/351 |
| 5,605,690 A | 2/1997 | Jacobs | |
| 5,610,279 A | 3/1997 | Brockhaus | |
| 5,639,597 A | 6/1997 | Lauffer | |
| 5,712,155 A | 1/1998 | Smith | |
| 5,808,029 A | 9/1998 | Brockhaus | |
| 5,945,397 A | 8/1999 | Smith | |
| 6,201,105 B1 | 3/2001 | Smith | |

FOREIGN PATENT DOCUMENTS

| | | | |
|---|---|---|---|
| EP | 325224 | 7/1989 | |
| EP | 0394827 | 4/1990 | |
| EP | 0422339 | 7/1990 | ........... C07K/13/00 |
| EP | 0417563 | 8/1990 | ........... C07K/15/12 |
| EP | 0433900 | 12/1990 | ........... C12N/15/12 |
| EP | 417563 | 3/1991 | |
| EP | 418014 | 3/1991 | |
| EP | 0460846 | 5/1991 | ........... C07K/13/00 |
| EP | 464533 | 6/1991 | |
| EP | 0526905 A2 | 2/1993 | ........... C12N/15/12 |
| WO | WO 8902922 | 4/1989 | |
| WO | WO 9108298 | 6/1991 | |
| WO | 91/1718 | * 11/1991 | ........... C07K/13/00 |

OTHER PUBLICATIONS

Parrillo, New Eng. J. of Med., 328(20):1471–1477 (1993), "Mech of DB–Pathogenic Mech. of Septic Shock".*

Dayer, J. Rheum. (suppl. 27) 18:71–75 (1991), "Chronic Inflam. Joint Diseases: Natural Inh. of 1L1 and TNF–2".*

Peppel et al, J. of Exp. Med., 174(6): 1483–1489 (1991) "A . . . TNF Receptor—IgG Heavy Chain Chimeric Protein as a Bivalent Antanonist . . . ".*

Seckinger et al. "Purification and Biologic Characterization of a Specific Necrosis Factor α Inhibitor" *J. Biol. Chem.* 264:11966–11973 (1989).

Loetscher et al., "Molecular Cloning and Expression of the Human 55 kd Tumor Necrosis Factor Receptor" *Cell* 61:351–359 (1990).

Engelmann et al., "Two Tumor Necrosis Factor–binding Proteins Purified from Human Urine" *B. Biol. Chem.* 265:1531–1536 (1990).

Hohmann et al., "Two Different Cell Types Have Different Major Receptors for Human Tumor Necrosis Factor (TNFα)" *J. Biol. Chem.* 264:14927–14934 (1989).

Peetre et al., "A tumor necrosis factor binding protein is present in human biological fluids" *Eur. J. Haematol.* 41:414–419 (1988).

Mohler et al., "Immunotherapeutic potential of soluble cytokine receptors in inflammatory disease" *The FASEB Journal* 6:A1123 (Mar. 11, 1992) ABSTR. 1086.

Goodwin et al., "Molecular Cloning and Expression of the Type 1 and Type 2 Murine Receptors for Tumor Necrosis Factor" *Mol. Cell. Biol.* 11:3020–3026 (Jun. 1991).

Sims et al., "Cloning the interleukin 1 receptor from human T cells" *Proc. Natl. Acad. Sci. USA* 86:8946–8950 (Nov. 1989).

Eisenberg et al., "Primary structure and functional expression from complementary DNA of a human interleukin–1 receptor antagonist" *Nature* 343:341–346 (Jan. 25, 1990).

(List continued on next page.)

Primary Examiner—Gary L. Kunz
(74) *Attorney, Agent, or Firm*—Sughrue Mion, PLLC; Gordon Kit

(57) ABSTRACT

Fusion proteins having a tumor necrosis factor receptor (TNF-R) polypeptide and at least one additional polypeptide covalently fused thereto and selected from an interleukin-1 receptor (IL-1R) and a second TNF-R polypeptide. The receptor polypeptides are preferably fused together by a peptidyl linker. Suitable fusions include, for example, TNF-R-linker-TNF-R; TNF-R-linker-IL-1R; and TNF-R-linker-TNF-R-linker-L-1R molecules.

30 Claims, 6 Drawing Sheets

OTHER PUBLICATIONS

Hannum et al., "Interleukin-1 receptor antagonist activity of a human interleukin-1 inhibitor" *Nature* 343:336–340 (Jan. 25, 1990).

Carter et al., "Purification, cloning, expression and biological characterization of an interleukin-1 receptor antagonist protein" *Nature* 344:633–638 (Apr. 12, 1990).

Seckinger et al., "A Human Inhibitor of Tumor Necrosis Factor β" *J. Exp. Med.* 167:1511–1516 (Apr. 1988).

U.S. application Serial No. 821,716, filed Jan. 14, 1992. (No copies needed.).

Heflin et al, "Prevention by Granulocyte Depletion of Increased Permeability of Sheep Lung following Endotoxemia". J. of Clin. Invest. v 68: 1253–1260 (Nov. 1981).

Eisenberg, S. et al., "Primary Structure and Functional Expression from Complementary DNA of a Human Interleukin-1 Receptor Antagonist", *Nature* 343:341–346, 1990.

Smith, C.A. et al., "A Receptor for Tumor Necrosis Factor Defines an Unusual Family of Cellular and Viral Proteins", *Science* 248:1019–1023, 1990.

Ashkenazi et al, *Proc. Natl. Acad. Sci., USA,* 88:10535–10539 (1991).

Capon et al, *Nature, 337*:525–530 (1989).

Evans et al, *J. Exp. Med., 180*:2173–2179 (1994).

Imamura et al, *J. Immunol., 139*:2989–2992 (1987).

Ishikura et al, *Blood, 73*:419–424 (1989).

Jones et al, *Nature, 338*:225–228 (1989).

Langner et al, *In: New Advances on Cytokines,* Eds. Romagnani et al, Raven Press, New York, pp. 349–354 (1992).

Lesslauer et al, *Eur. J. Immunol., 21*:2883–2886 (1991).

Loetscher et al, *J. Biol. Chem., 266*:18324–18239 (1991).

Mohler et al, *J. Immunol., 151*:1548–1561 (1993).

Peppel et al, *J. Cell Biochem. Supp., 0(15 Part F)* :118 (1991).

Peppel et al, *J. Exp. Med., 174*:1483–1489 (1991).

Rutka et al, *Int. J. Cancer Res., 41*:573–582 (1988).

Smith et al, *J. Biol. Chem., 262*:6951–6954 (1987).

Smith et al., *Science, 248*:1019–1023 (1990).

Dembic et al, *Cytokine, 2*:231–237 (1990).

Kohno et al, *Proc. Natl. Acad. Sci., USA, 87*:8331–8335 (1990).

Nophar et al, *Embo J., 9*:3269–3278 (1990).

Schall et al, *Cell, 61*:361–370 (1990).

* cited by examiner

FIGURE 2

```
                                             GCGAGGCAGGCAGCCTGGAGAGAAGGCG      23
CTGGGCTGCGAGGGCGCGAGGGCGCGAGGGCAGGGGGCAACCGGACCCCGCCCGCATCC                    87
ATG GCG CCC GTC GCC GTC TGG GCC GCG CTG GCC GTC GGA CTG GAG                   132
Met Ala Pro Val Ala Val Trp Ala Ala Leu Ala Val Gly Leu Glu                    -8
                                                ↓BglI
CTC TGG GCT GCG GCG CAC GCC TTG CCC GCC CAG GTG GCA TTT ACA                   177
Leu Trp Ala Ala Ala His Ala Leu Pro Ala Gln Val Ala Phe Thr                     8
CCC TAC GCC CCG GAG CCC GGG AGC ACA TGC CGG CTC AGA GAA TAC                   222
Pro Tyr Ala Pro Glu Pro Gly Ser Thr Cys Arg Leu Arg Glu Tyr                    23
TAT GAC CAG ACA GCT CAG ATG TGC TGC AGC AAA TGC TCG CCG GGC                   267
Tyr Asp Gln Thr Ala Gln Met Cys Cys Ser Lys Cys Ser Pro Gly                    38
CAA CAT GCA AAA GTC TTC TGT ACC AAG ACC TCG GAC ACC GTG TGT                   312
Gln His Ala Lys Val Phe Cys Thr Lys Thr Ser Asp Thr Val Cys                    53
GAC TCC TGT GAG GAC AGC ACA TAC ACC CAG CTC TGG AAC TGG GTT                   357
Asp Ser Cys Glu Asp Ser Thr Tyr Thr Gln Leu Trp Asn Trp Val                    68
CCC GAG TGC TTG AGC TGT GGC TCC CGC TGT AGC TCT GAC CAG GTG                   402
Pro Glu Cys Leu Ser Cys Gly Ser Arg Cys Ser Ser Asp Gln Val                    83
GAA ACT CAA GCC TGC ACT CGG GAA CAG AAC CGC ATC TGC ACC TGC                   447
Glu Thr Gln Ala Cys Thr Arg Glu Gln Asn Arg Ile Cys Thr Cys                    98
                              ↓EspI
AGG CCC GGC TGG TAC TGC GCG CTG AGC AAG CAG GAG GGG TGC CGG                   492
Arg Pro Gly Trp Tyr Cys Ala Leu Ser Lys Gln Glu Gly Cys Arg                   113
CTG TGC GCG CCG CTG CGC AAG TGC CGC CCG GGC TTC GGC GTG GCC                   537
Leu Cys Ala Pro Leu Arg Lys Cys Arg Pro Gly Phe Gly Val Ala                   128
AGA CCA GGA ACT GAA ACA TCA GAC GTG GTG TGC AAG CCC TGT GCC                   582
Arg Pro Gly Thr Glu Thr Ser Asp Val Val Cys Lys Pro Cys Ala                   143
                                                     ↑
CCG GGG ACG TTC TCC AAC ACG ACT TCA TCC ACG GAT ATT TGC AGG                   627
Pro Gly Thr Phe Ser Asn Thr Thr Ser Ser Thr Asp Ile Cys Arg                   158
CCC CAC CAG ATC TGT AAC GTG GTG GCC ATC CCT GGG AAT GCA AGC                   672
Pro His Gln Ile Cys Asn Val Val Ala Ile Pro Gly Asn Ala Ser                   173
                    ↑
ATG GAT GCA GTC TGC ACG TCC ACG TCC CCC ACC CGG AGT ATG GCC                   717
Met Asp Ala Val Cys Thr Ser Thr Ser Pro Thr Arg Ser Met Ala                   188
                                                     ↑
CCA GGG GCA GTA CAC TTA CCC CAG CCA GTG TCC ACA CGA TCC CAA                   762
Pro Gly Ala Val His Leu Pro Gln Pro Val Ser Thr Arg Ser Gln                   203
CAC ACG CAG CCA ACT CCA GAA CCC AGC ACT GCT CCA AGC ACC TCC                   807
His Thr Gln Pro Thr Pro Glu Pro Ser Thr Ala Pro Ser Thr Ser                   218
                                             ↓PvuII
TTC CTG CTC CCA ATG GGC CCC AGC CCC CCA GCT GAA GGG AGC ACT                   852
Phe Leu Leu Pro Met Gly Pro Ser Pro Pro Ala Glu Gly Ser Thr                   233
```

FIGURE 2 Cont'd.

```
GGC GAC TTC GCT CTT CCA GTT GGA CTG ATT GTG GGT GTG ACA GCC      897
Gly Asp Phe Ala Leu Pro Val Gly Leu Ile Val Gly Val Thr Ala      248
        ↑
TTG GGT CTA CTA ATA ATA GGA GTG GTG AAC TGT GTC ATC ATG ACC      942
Leu Gly Leu Leu Ile Ile Gly Val Val Asn Cys Val Ile Met Thr      263

CAG GTG AAA AAG AAG CCC TTG TGC CTG CAG AGA GAA GCC AAG GTG      987
Gln Val Lys Lys Lys Pro Leu Cys Leu Gln Arg Glu Ala Lys Val      278

CCT CAC TTG CCT GCC GAT AAG GCC CGG GGT ACA CAG GGC CCC GAG     1032
Pro His Leu Pro Ala Asp Lys Ala Arg Gly Thr Gln Gly Pro Glu      293

CAG CAG CAC CTG CTG ATC ACA GCG CCG AGC TCC AGC AGC AGC TCC     1077
Gln Gln His Leu Leu Ile Thr Ala Pro Ser Ser Ser Ser Ser Ser      308

CTG GAG AGC TCG GCC AGT GCG TTG GAC AGA AGG GCG CCC ACT CGG     1122
Leu Glu Ser Ser Ala Ser Ala Leu Asp Arg Arg Ala Pro Thr Arg      323

AAC CAG CCA CAG GCA CCA GGC GTG GAG GCC AGT GGG GCC GGG GAG     1167
Asn Gln Pro Gln Ala Pro Gly Val Glu Ala Ser Gly Ala Gly Glu      338

GCC CGG GCC AGC ACC GGG AGC TCA GAT TCT TCC CCT GGT GGC CAT     1212
Ala Arg Ala Ser Thr Gly Ser Ser Asp Ser Ser Pro Gly Gly His      353

GGG ACC CAG GTC AAT GTC ACC TGC ATC GTG AAC GTC TGT AGC AGC     1257
Gly Thr Gln Val Asn Val Thr Cys Ile Val Asn Val Cys Ser Ser      368

TCT GAC CAC AGC TCA CAG TGC TCC TCC CAA GCC AGC TCC ACA ATG     1302
Ser Asp His Ser Ser Gln Cys Ser Ser Gln Ala Ser Ser Thr Met      383

GGA GAC ACA GAT TCC AGC CCC TCG GAG TCC CCG AAG GAC GAG CAG     1347
Gly Asp Thr Asp Ser Ser Pro Ser Glu Ser Pro Lys Asp Glu Gln      398

GTC CCC TTC TCC AAG GAG GAA TGT GCC TTT CGG TCA CAG CTG GAG     1392
Val Pro Phe Ser Lys Glu Glu Cys Ala Phe Arg Ser Gln Leu Glu      413

ACG CCA GAG ACC CTG CTG GGG AGC ACC GAA GAG AAG CCC CTG CCC     1437
Thr Pro Glu Thr Leu Leu Gly Ser Thr Glu Glu Lys Pro Leu Pro      428

CTT GGA GTG CCT GAT GCT GGG ATG AAG CCC AGT                    1470
Leu Gly Val Pro Asp Ala Gly Met Lys Pro Ser                     439

TAACCAGGCCGGTGTGGGCTGTGTCGTAGCCAAGGTGGGCTGAGCCCTGGCAGGATGAC

CCTGCGAAGGGGCCCTGGTCCTTCCAGGCCCCCACCACTAGGACTCTGAGGCTCTTTCT

GGGCCAAGTTCCTCTAGTGCCCTCCACAGCCGCAGCCTCCCTCTGACCTGCAG....
```

FUSION PROTEINS COMPRISING TUMOR NECROSIS FACTOR RECEPTOR

CROSS-REFERENCE TO RELATED APPLICATION

This is a continuation of application Ser. No. 08/255,849, filed Jun. 8, 1994, now abandoned, which application is a continuation-in-part of U.S. application Ser. No. 523,635, filed May 10, 1990, now U.S. Pat. No. 5,395,760 is a continuation-in-part of U.S. application Ser. No. 07/421,417, filed Oct. 13, 1989, now abandoned, which is a continuation-in-part of U.S. application Ser. No. 07/405,370, filed Sep. 11, 1989, now abandoned, which is a continuation-in-part of U.S. application Ser. No. 07/403,241, filed Sep. 5, 1989, now abandoned, which prior applications are all incorporated by reference in their entirety.

BACKGROUND OF THE INVENTION

A number of cytokines are known to bind to specific receptor proteins on the surface of target cells. Among the specific receptor proteins that have been identified are tumor necrosis factor receptors and interleukin-1 receptors. Much effort is being directed toward isolation and characterization of a number of receptors in order to study their physiological roles and to explore possible therapeutic uses. The binding of a particular target molecule by a soluble receptor administered to a patient may alleviate disorders mediated by the target molecule.

Tumor necrosis factor-α (TNFα, also known as cachectin) and tumor necrosis factor-β (TNFβ, also known as lymphotoxin) are homologous mammalian endogenous secretory proteins capable of inducing a wide variety of effects on a large number of cell types. The great similarities in the structural and functional characteristics of these two cytokines have resulted in their collective description as "TNF." Complementary cDNA clones encoding TNFα (Pennica et al., *Nature* 312:724, 1984) and TNFβ (Gray et al., *Nature* 312:721, 1984) have been isolated, permitting further structural and biological characterization of TNF.

TNF proteins initiate their biological effect on cells by binding to specific TNF receptor (TNF-R) proteins expressed on the plasma membrane of a TNF-responsive cell. TNFα and TNFβ were first shown to bind to a common receptor on the human cervical carcinoma cell line ME-180 (Aggarwal et al., *Nature* 318:665, 1985). Hohmann et al. (*J. Biol. Chem.* 264:14927, 1989) reported that at least two different cell surface receptors for TNF exist on different cell types, although the relationship between these TNF-Rs is unclear. These receptors have an apparent molecular mass of about 75–80 kDa and about 55–60 kDa, respectively. In addition to cell surface receptors for TNF, soluble proteins from human urine capable of binding TNF have also been identified (Peetre et al., *Eur. J. Haematol.* 41:414, 1988; Seckinger et al., *J. Exp. Med.* 167:1511, 1988; Seckinger et al., *J. Biol. Chem.* 64:11966, 1989; UK Patent Application, Publ. No. 2 218 101 A to Seckinger et al.; Engelmann et al., *J. Biol. Chem.* 264:11974, 1989).

Interleukin-1α (IL-1α) and interleukin-1β (IL-1β) are distantly related polypeptide hormones that play a central role in the regulation of immune and inflammatory responses. These two proteins act on a variety of cell types and have multiple biological activities. The biological activities ascribed to IL-1α and IL-1β are mediated via at least two classes of plasma membrane bound receptors which bind both IL-1α and IL-1β. The IL-1 receptors expressed on B cells (referred to herein as type II IL-1 receptors) are different from IL-1 receptors detected on T cells and other cell types (referred to herein as type I IL-1 receptors).

SUMMARY OF THE INVENTION

The present invention is directed to receptors comprising a first tumor necrosis factor receptor (TNF-R) polypeptide covalently linked to a second TNF-R polypeptide. Alternatively, the receptor comprises one or two TNF-R polypeptides covalently linked to one or two interleukin-1 receptor (IL-1R) polypeptides.

The receptors preferably are produced as fusion proteins via recombinant DNA technology. The present invention provides fusion proteins comprising, as one of at least two biologically active polypeptide components, a TNF-R polypeptide. One fusion protein of the present invention comprises two TNF-R polypeptides, preferably joined via a peptide linker.

In another embodiment of the invention, the fusion protein comprises TNF-R and IL-1R. The fusion protein preferably comprises two TNF-R polypeptides and either one or two IL-1R polypeptides.

The present invention also provides isolated DNA sequences encoding the fusion proteins, recombinant expression vectors comprising such DNA sequences, host cells containing the expression vectors, and processes for producing the recombinant fusion proteins by culturing the host cells. Pharmaceutical compositions comprising a purified fusion protein as described above and a suitable diluent, carrier, or excipient are also provided by the present invention. Such compositions are useful in therapy, diagnosis, and assays for conditions mediated by tumor necrosis factor or interleukin-1.

BRIEF DESCRIPTION OF THE DRAWINGS

FIG. 2 depicts the partial cDNA sequence and derived amino acid sequence of a human TNF-R clone. Nucleotides are numbered from the beginning of the 5' untranslated region. Amino acids are numbered from the beginning of the signal peptide sequence. The apparent signal peptide sequence is represented by the amino acids −22 to −1. The N-terminal leucine of the mature TNF-R protein is underlined at position 1. The apparent transmembrane region from amino acids 236 to 265 is also underlined. The C-termini of various soluble TNF-Rs are marked with an arrow (↕). Cleavage sites for certain restriction endonucleases employed in constructing expression vectors are indicated.

DETAILED DESCRIPTION OF THE INVENTION

Figure 1:
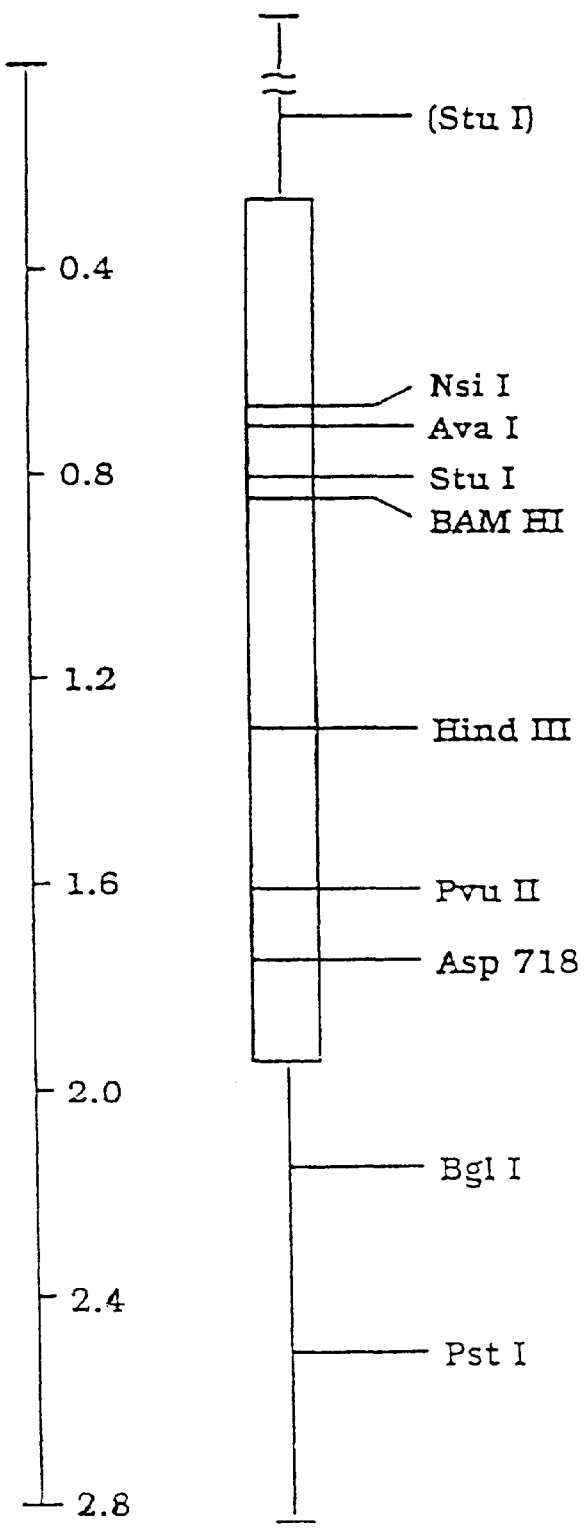
FIG. 1 presents a restriction map for a type I human IL-1R cDNA clone. The sites at which certain restriction enzymes cleave the cDNA are shown.

Both monovalent forms and polyvalent forms of TNF-R are useful in the compositions and methods of this invention.

Polyvalent forms possess multiple TNF-R binding sites for TNF ligand. For example, a bivalent soluble TNF-R may consist of two tandem repeats of amino acids 1–235 of FIG. 2, separated by a linker region. Alternate polyvalent forms may also be constructed, for example, by chemically coupling TNF-R to any clinically acceptable carrier molecule, a polymer selected from the group consisting of Ficoll, polyethylene glycol or dextran using conventional coupling techniques. Alternatively TNF-R may be chemically coupled to biotin, and the biotin-TNF-R conjugate then allowed to bind to avidin, resulting in tetravalent avidin/biotin/TNF-R molecules. TNF-R may also be covalently coupled to dinitrophenol (DNP) or trinitrophenol (TNP) and the resulting conjugate precipitated with anti-DNP or anti-TNP-IgM, to form decameric conjugates with a valency of 10 for TNF-R binding sites.

A recombinant chimeric antibody molecule may also be produced having TNF-R sequences substituted for the variable domains of either or both of the immunoglobulin molecule heavy and light chains and having unmodified constant region domains. For example, chimeric TNF-R/IgG$_1$ may be produced from two chimeric genes—a TNF-R/human k light chain chimera (TNF-R/C$_k$) and a TNF-R/human $\gamma_1$ heavy chain chimera (TNF-R/C$_{\gamma-1}$). Following transcription and translation of the two chimeric genes, the gene products assemble into a single chimeric antibody molecule having TNF-R displayed bivalently. Such polyvalent forms of TNF-R may have enhanced binding affinity for TNF ligand. Additional details relating to the construction of such chimeric antibody molecules are disclosed in WO 89/09622 and EP 315062.

The present invention is directed to receptors comprising a first TNF-R polypeptide covalently linked to a second TNF-R polypeptide. Alternatively, the receptor comprises one or two TNF-R polypeptides covalently linked to one or two IL-1R polypeptides. The TNF-R and (when present) IL-1R polypeptide components may be attached to one another using any suitable technique for attaching one polypeptide to another. Cross-linking reagents and peptide linkers are among the linkage methods that may be employed. The TNF-R and IL-1R polypeptides are derived from mammalian species, preferably human.

The receptors preferably are produced as fusion proteins via recombinant DNA technology. The present invention provides fusion proteins comprising, as one component, a mammalian tumor necrosis factor receptor (TNF-R). One fusion protein of the present invention comprises two TNF-R polypeptides and may be represented by the following formula:

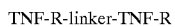

wherein the linker is a peptide linker.

In another embodiment of the invention, the fusion protein comprises TNF-R and a mammalian interleukin-1 receptor (IL-1R). In this embodiment of the invention, the fusion protein may comprise one TNF-R polypeptide and one IL-1R polypeptide. Preferably, two TNF-R polypeptides and one IL-1R polypeptide are joined to form the fusion protein. The two TNF-R polypeptides preferably are adjacent to one another (as opposed to IL-1R being positioned between the two TNF-Rs) to enhance binding of TNF. Examples of such fusion proteins are represented by the following formulas:

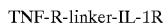

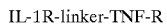

and

wherein each linker is a peptide linker. The N-terminus of each fusion protein is on the left side of each formula.

Each TNF-R polypeptide component of the fusion proteins is independently capable of binding tumor necrosis factor (TNF). Likewise, each IL-1R polypeptide employed in the fusion proteins is independently capable of binding interleukin-1 (IL-1). Including two adjacent TNF-R polypeptides in the fusion protein is advantageous in that the TNF binding affinity is increased compared to the binding of TNF by a single TNF-R polypeptide.

Peptide linkers that may be employed in the present invention separate TNF-R polypeptides (and IL-1R polypeptides, when present) from one another by a distance sufficient to ensure that each polypeptide properly folds into the secondary and tertiary structures necessary for the desired biological activity. The linker also should allow the extracellular domains of the TNF-R and IL-1R polypeptides to assume the proper spatial orientation to form a binding site for TNF or IL-1. The peptide linkers function as spacers, as opposed to the pharmaceutically active TNF-R and IL-1R polypeptide components of the fusion proteins. Suitable polypeptide linkers preferably (1) will adopt a flexible extended conformation, (2) will not exhibit a propensity for developing an ordered secondary structure which could interact with the functional protein domains, and (3) will have minimal hydrophobic or charged character which could promote interaction with the functional protein domains. Typical surface amino acids in flexible protein regions include glycine (Gly), asparagine (Asn) and serine (Ser). Virtually any permutation of amino acid sequences containing Gly, Asn and Ser would be expected to satisfy the above criteria for a peptide linker sequence. Other near neutral amino acids, such as threonine (Thr) and alanine (Ala), may also be used in the linker sequence. Suitable peptide linkers generally comprise a chain of amino acids, preferably from 5 to 100 amino acids in length and most preferably from 10 to 20 amino acids in length. Examples of such linkers include, but are not limited to (Gly$_4$Ser (SEQ ID NO:22))$_n$, wherein n is 1–12, Gly$_4$SerGly$_5$Ser (SEQ ID NO:23), and (Gly$_4$SerGly$_5$Ser)$_2$ (SEQ ID NO:24).

TNF-R and IL-1R Polypeptides

As used herein, the terms "interleukin-1 receptor" and "IL-1R" refer to proteins which are capable of binding interleukin-1 (IL-1) molecules and, in their native configuration as human plasma membrane proteins, play a role in transducing the signal provided by IL-1 to a cell. As used herein, the terms "TNF receptor" and "TNF-R" refer to proteins that are biologically active in that they are capable of binding tumor necrosis factor (TNF). Native membrane bound forms of the proteins also transduce a biological signal initiated by a TNF molecule binding to a cell. For fusion proteins comprising more than one TNF-R polypeptide, the TNF-R polypeptides may be identical or different. Likewise for IL-1R polypeptides.

Intact receptors generally include an extracellular domain which binds to a ligand, a hydrophobic transmembrane domain which remains embedded within the plasma membrane lipid bilayer, and a cytoplasmic or intracellular domain which is believed to deliver a biological signal to effector cells via a cascade of chemical reactions within the cytoplasm of the cell. The hydrophobic transmembrane domain and a highly charged region of the cytoplasmic domain immediately downstream of the transmembrane domain cooperatively function to halt transport of the IL-1 and TNF receptors across the plasma membrane. The extracellular domain of the TNF-R and IL-1R proteins disclosed herein is the N-terminal portion of the protein, from amino acid 1 to the amino acid immediately preceding the transmembrane region. The cytoplasmic domain is that portion of the protein that is located downstream of the transmembrane region.

Among the TNF-R polypeptides that may be employed as components of the inventive fusion proteins is a polypeptide comprising amino acids 1 to 439 of the sequence presented in FIG. 2, which is a full length native TNF-R sequence. This TNF-R DNA and amino acid sequence is also presented in SEQ ID NOS: 1 and 2. When the signal sequence is desired, the TNF-R polypeptide may comprise amino acids −22 to 439 of the FIG. 2 sequence. The desirability of including the signal sequence depends on such factors as the position of the TNF-R polypeptide in the fusion protein and whether the intended host cells will process a mammalian signal sequence, as discussed below. The mature full-length native glycosylated form of this human TNF-R is a glycoprotein having a molecular weight of about 80 kilodaltons (kDa). As used throughout the specification, the term "mature" means a protein lacking a leader or signal sequence as may be present in full-length transcripts of a native gene. A protein may comprise a signal sequence when initially expressed. Cleavage of the signal sequence upon secretion of the protein from the cell yields the mature form of the protein.

Other suitable TNF-R polypeptides are described in European patent application publication number 422,339 (EP 422,339 hereinafter), which is hereby incorporated by reference in its entirety. Two suitable TNF-R polypeptides comprise arginine (Arg) as residue 174 but are otherwise identical to the above-described polypeptides comprising amino acids 1 to 439 or −22 to 439, respectively, of FIG. 2 of the present application. A TNF-R amino acid sequence identical to that of FIG. 2 (of the present application) except for substitution of arginine (Arg) for methionine (Met) at position 174 of the mature sequence is disclosed in EP 422,339 (see FIG. 39 therein).

The cDNA and encoded amino acid sequences of another useful TNF-R polypeptide are disclosed in FIG. 21 of EP 422,339. The coding region of the EP 422,339 FIG. 21 cDNA sequence, and the amino acid sequence encoded thereby, are presented as SEQ ID NOS: 3 and 4 of the present application. Although referred to as a 30 kilodalton protein in EP 422,339, other molecular weights have been reported for this protein. A molecular weight of about 55 kilodaltons was reported by Loetscher et al. (*Cell* 61:351, 1990) and in EP 417,563, for example. Useful TNF-R polypeptides include those comprising amino acids 1 to 415 of the SEQ ID NO:4 sequence, or, when the signal sequence is desired, amino acids −40 to 415 of the SEQ ID NO:4 sequence. Methods for producing this TNF-R protein, either by purification from urine or from the medium of a culture of U937 cells, or by recombinant DNA technology, are described in EP 422,339. This TNF-R is characterized by an N-terminal sequence (for the mature form of the protein) of Asp-Ser-Val-Cys-Pro-Gln- (SEQ ID NO:25), whereas the N-terminal sequence of the mature form of the TNF-R protein of FIG. 2 is Leu-Pro-Ala-Gln-Val-Ala- (SEQ ID NO:26).

In certain embodiments of the present invention, the TNF-R polypeptide is a soluble TNF-R polypeptide. Soluble TNF-R polypeptides lack at least part (preferably all) of the transmembrane region that promotes retention of the protein on the cell surface. The soluble polypeptides generally also lack the charged region of the cytoplasmic domain (located immediately downstream of the transmembrane region) that contributes to retention on the cell surface. Preferably, the entire transmembrane region and cytoplasmic domain are deleted from the protein or substituted with hydrophilic amino acids to form soluble TNF-R. Soluble TNF-R is secreted from the cell and retains the desired biological activity.

Examples of soluble TNF-R polypeptides are those comprising amino acids 1–x of the FIG. 2 sequence, wherein x is the C-terminal amino acid and is selected from the group consisting of any one of amino acids 163–235 of FIG. 2. Specific examples include polypeptides comprising the acids 1–163, 1–185, or 1–235 of FIG. 2. The soluble TNF-R polypeptide may additionally comprise a signal sequence, e.g., amino acids −22 to −1 of FIG. 2.

Additional examples of soluble TNF-R polypeptides are those comprising amino acids 1–184 or 1–182, −22–184, or −22–182 of the FIG. 2 sequence. Such proteins may contain either methionine or arginine at position 174. Procedures for preparing examples of such TNF-R polypeptides include those described in examples 17 and 22 of EP 422,339.

The TNF-R protein shown in SEQ ID NO:4 comprises a signal peptide (designated amino acids −40 to −1) and a transmembrane region beginning with the valine residue at position 172. Preferred soluble forms of this TNF-R protein include those comprising amino acids −40–w or 1–w of SEQ ID NO:4, wherein w is an integer from 161–171 (i.e., any of amino acids 161 to 171 of SEQ ID NO:4 is the C-terminus). The use of oligonucleotide-directed in vitro mutagenesis to construct an expression vector encoding a biologically active TNF-R protein having amino acid 161 (asparagine) as the C-terminal amino acid is illustrated in example 7 of EP 422,339. Further, procedures for purifying naturally occurring soluble forms of both of the above-described TNF-R proteins (i.e., soluble forms of the SEQ ID NO:2 and the SEQ ID NO:4 proteins) from human urine have been described by Engelmann et al. (*J. Biol. Chem.* 265:1531, 1990).

Interleukin-1 receptors that may be employed as components of the inventive fusion proteins include polypeptides designated herein as type I IL-1R and type II IL-1R. Type I IL-1 receptors have been detected on T-cells and certain other cell types, while expression of type II IL-1 receptors on B cells has been reported. In the absence of any specific designation, the term "IL-1 receptor" as used herein refers collectively to type I and type II IL-1 receptors.

Among the IL-1R polypeptides that may be employed in the present invention are the type I IL-1R polypeptides described in U.S. patent application Ser. No. 07/821,716, filed Jan. 14, 1992; and Ser. No. 455,488, filed Dec. 21, 1989; and in European patent application publication no. 318,296; the disclosures of which are incorporated herein by reference, in their entireties. The DNA sequence of a cloned cDNA encoding a human type I IL-1R protein and the amino acid sequence encoded thereby are presented herein in SEQ ID NOS: 5 and 6. The protein contains 569 amino acids, of which 20 are an N-terminal signal peptide. The aspartic acid (Asp) residue at position 1 is the first amino acid of the mature protein. The transmembrane region includes amino acids 317 (His) through 336 (Tyr). The sequence of human IL-1R is also disclosed in Sims et al., *Proc Nat'l. Acad. Sci. USA* 86:8946 (1989).

As with the TNF-R polypeptides, soluble IL-1R polypeptides may be employed in the fusion proteins of the present invention. Soluble IL-1R polypeptides generally lack the transmembrane region and preferably lack the cytoplasmic domain as well. Soluble IL-1R proteins may also include part of the transmembrane region or the cytoplasmic domain, provided that the soluble IL-1R protein is capable of being secreted from the cell.

Examples of soluble type I IL-1R polypeptides include, but are not limited to, those comprising the amino acid sequence depicted as amino acids y-x of SEQ ID NO: 6, wherein x is 312–316 and y is −3 to 3. In other words, the N-terminal amino acid is selected from the Leu, Glu, Ala, Asp, Lys, and Cys residues at positions −3, −2, −1, 1, 2, and 3, respectively. The C-terminal amino acid of the soluble protein is selected from the Thr, Asn, Phe, Gln, and Lys residues at positions 312, 313, 314, 315, and 316, respectively. Preferred soluble IL-1R polypeptides include those comprising amino acids 1–x of SEQ ID NO: 6, wherein x is 312–316.

Any of the above-described soluble type I IL-1R polypeptides may additionally comprise a signal sequence, e.g., the signal sequence shown as amino acids −20 to −1 in SEQ ID NO: 6. Alternatively, a different signal sequence functional in an intended host cell (e.g., a yeast signal sequence) may be employed, as discussed below.

Among the type II IL-1R polypeptides that may be employed in the present invention are those described in U.S. patent application Ser. No. 701,415, filed Jun. 16, 1991; and in European patent application publication no. 460,846; the disclosures of which are incorporated herein by reference, in their entireties. Native glycosylated human type II IL-1R proteins recovered from cell lysates generally have an apparent molecular weight of about 60–68 kilodaltons by SDS-PAGE. The DNA sequence of a cloned cDNA encoding a human type II IL-1R protein and the amino acid sequence encoded thereby are presented herein in SEQ ID NOS: 7 and 8. The protein comprises a 13-amino acid signal peptide. The transmembrane region includes amino acids 331 (Ala) through 356 (Met).

Soluble type II IL-1R proteins are derived by deleting a C-terminal portion of the protein that is not necessary for IL-1 binding, so that the protein is secreted from the cell. The cysteine residue at position 313 is believed to be necessary to maintain the tertiary structure of the type II IL-1R molecule and permit binding of IL-1. Examples of soluble type II IL-1R polypeptides thus include those in which the C-terminal amino acid is selected from any of amino acids 314–333. In other words, the soluble IL-1R may contain the amino acid sequence shown as amino acids 1–x of SEQ ID NO: 8 wherein x is an integer from 314–333. Preferred examples of suitable soluble type II IL-1R polypeptides include, but are not limited to, those comprising amino acids 1–x of SEQ ID NO: 8, wherein x is 330–333. In other words, the C-terminal amino acid of the soluble protein is selected from the Glu, Ala, Ser, and Ser residues at positions 330, 331, 332, and 333, respectively. The soluble type II IL-1R polypeptides may additionally comprise a signal sequence, e.g., the signal sequence shown as amino acids −13 to −1 in SEQ ID NO: 8. Alternatively, a different signal sequence functional in an intended host cell (e.g., a yeast signal sequence) may be employed, as discussed below.

Assay procedures described herein may be employed to confirm biological activity for additional soluble TNF-R and IL-1R polypeptides, beyond the particular examples set forth above. Soluble TNF-R and soluble IL-1R may be identified (and distinguished from their non-soluble membrane-bound counterparts) by separating intact cells which express the desired protein from the culture medium, e.g., by centrifugation, and assaying the medium (supernatant) for the presence of the desired protein. The culture medium may be assayed using procedures which are similar or identical to those described in the examples below. The presence of TNF-R and IL-1R in the medium indicates that the protein was secreted from the cells and thus is a soluble form of the desired protein.

The N- or C-terminus of the TNF-R or IL-1 R polypeptides may vary according to such factors as the type of host cells employed when producing the fusion protein via recombinant DNA technology and the particular cells from which the protein is purified when non-recombinant TNF-R or IL-1R is employed. Such variations may be attributable to differential post-translational processing of the protein in various types of cells, for example. Variations in the N- or C-terminal sequence also may result from the oligonucleotides chosen to reconstruct either terminus of the TNF-R or IL-1R encoding DNA sequence when constructing expression vectors.

Differential processing may result in mature TNF-R or IL-1R proteins having an N-terminal amino acid other than those shown at position 1 of SEQ ID NOS: 2, 4, 6 and 8. For example, in certain host cells, post-translational processing will remove the methionine residue encoded by an initiation codon, whereas the methionine residue will remain at the N-terminus of proteins produced in other host cells. Further, the N- and C-termini have been known to vary for the same protein, depending on the source of the protein. In some cases, the deletion of amino acids at either terminus of the protein may be due to proteolysis, occurring either intracellularly or during purification. Varying N-termini may also result from cleavage of the signal peptide in certain host cells at a point other than between amino acids −1 and 1 of the disclosed sequences.

As described in examples 10 and 11 and FIG. 31 of EP 422,339, a non-recombinant mature TNF-R protein purified from human urine lacked two N-terminal amino acids found in a non-recombinant TNF-R protein purified from the human monocyte-like cell line U937. The N-terminal amino acid of the urine-derived TNF-R was the alanine residue at position 3 of SEQ ID NO:1. Engelmann et al. (*J. Biol. Chem.* 265:1531, 1990) disclose a protein that binds TNF and was purified from human urine in forms truncated to varying degrees at the N-terminus (see the abstract and page 1533). The N-terminal amino acid sequence of one protein species was Val-Ala-Phe-Thr-Pro- (SEQ ID NO:27), which corresponds to amino acids 5–9 of SEQ ID NO:1. Other forms of the protein. had either phenylalanine (amino acid 7 of SEQ ID NO:1) or threonine (amino acid 8 of SEQ ID NO:1) as the N-terminal amino acid.

The N- and C-termini of the TNF-R and IL-1R proteins may vary for reasons that include those discussed above. The N-terminal amino acid may, for example, be any of the amino acids at positions 1 to 5 of SEQ ID NOS: 2 or 4 for TNF-R or of SEQ ID NOS: 6 or 8 for IL-1R. The C-terminus may be truncated deliberately during expression vector construction (e.g., in constructing vectors encoding soluble proteins as described above) or as a result of differential processing which may remove up to about five C-terminal amino acids, for example.

Additional TNF-R and IL-1R polypeptides that may be employed retain the desired biological activity but vary from the native sequences in that amino acid(s) are added to, deleted from, or substituted in the native sequence. The biological activity of such proteins can be confirmed using the assays described herein.

Derivatives of TNF-R and IL-1R that are within the scope of the invention also include various structural forms of the primary protein which retain biological activity. Due to the presence of ionizable amino and carboxyl groups, for example, a TNF-R or IL-1R protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like. Covalent derivatives are prepared by linking particular functional groups to amino acid side chains or at the N- or C-termini. Naturally occurring variants may result from alternative RNA splicing events.

Other proteins that may be employed in the inventive fusion proteins include conjugates of TNF-R or IL-1R with other polypeptides, which may be produced by synthesis in recombinant culture as N-terminal or C-terminal fusions. For example, the conjugated peptide may be a a signal (or leader) peptide sequence at the N-terminal region of the protein which co-translationally or post-translationally directs transfer of the protein from its site of synthesis to its site of function inside or outside of the cell membrane or wall (e.g., the yeast α-factor leader). The fusion proteins can comprise peptides added to facilitate purification or identification of the fusion protein. Such peptides include, for example, poly-His or the antigenic identification peptides described in U.S. Pat. No. 5,011,912 and in Hopp et al., *Bio/Technology* 6:1204,1988. One such peptide is the FLAG® peptide, Asp-Tyr-Lys-Asp-Asp-Asp-Asp-Lys (DYKDDDDK (SEQ ID NO:28)), which is highly antigenic and provides an epitope reversibly bound by a specific monoclonal antibody enabling rapid assay and facile purification or expressed recombinant protein. This sequence is also specifically cleaved by bovine mucosal enterokinase at the residue intermediately following the Asp-Lys pairing. Fusion proteins capped with this peptide may also be resistant to intracellular degradation in *E. coli*. A murine hybridoma designated 4E11 producers a monoclonal antibody that binds the peptide DYKDDDDK (SEQ ID NO:28) in the presence of certain divalent metal cations (as described in U.S. Pat. No. 5,011,912) and has been deposited in the American Type Culture Collection under accession no. HB 9259.

The inventive fusion proteins comprise TNF-R or IL-1R with or without associated native-pattern glycosylation. TNF-R and IL-1R expressed in yeast or mammalian expression systems, e.g., COS-7 cells, may be similar or slightly different in molecular weight and glycosylation pattern than the native molecules, depending upon the expression system. Expression of recombinant proteins in bacteria such as *E. coli* provides non-glycosylated proteins. Proteins having inactivated N-glycosylation sites can be produced by oligonucleotide synthesis and ligation or by site-specific mutagenesis techniques. These mutant proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$. Known procedures for inactivating N-glycosylation sites in proteins include those described in U.S. Pat. No. 5,071,972 and EP 276,846. Examples of N-glycosylation sites in human type II IL-1R are amino acids 53–55, 59–61, 99–101, 206–208, and 264–266 in SEQ ID NO: 8. Potential N-glycosylation sites are found in the type I IL-1R protein (SEQ ID NO: 6) at amino acids 80–82, 173–175, 213–215, 229–231, 243–245, and 277–279. N-glycosylation sites are found at amino acid 171–173 and 358–360 of TNF-R in FIG. 2.

Cysteine residues that are not essential for biological activity can be deleted or replaced with other amino acids to prevent formation of unnecessary or incorrect intramolecular disulfide bridges upon renaturation. The cysteine residue at position 178 in the FIG. 2 TNF-R sequence can be deleted, for example. U.S. Pat. No. 4,518,584 describes the use of site directed mutagenesis to delete or replace cysteine residues within a protein. Other approaches to mutagenesis involve modification of adjacent dibasic amino acid residues to enhance expression in yeast systems in which KEX2 protease activity is present. EP 212,914 discloses the use of site-specific mutagenesis to inactivate KEX2 protease processing sites in a protein.

In order to preserve the biological activity of TNF-R and IL-1R, substitutions will preferably result in homologous or conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian TNF-Rs is suggestive of additional conservative substitutions that may be made without altering the essential biological characteristics of TNF-R or IL-1R.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods,* Plenum Press, 1981); and U.S. Patent Nos. 4,518, 584 and 4,737,462 disclose suitable techniques, and are incorporated by reference herein.

The variant amino acid sequence preferably is at least 80% identical, most preferably at least 90% identical, to the native sequence. Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math. 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps.

Other proteins capable of blocking the binding of IL-1 to cellular receptors in vivo may be substituted for the IL-1R polypeptides described above in the fusion proteins of the present invention. Such proteins, generally referred to as IL-1 receptor antagonists, include those described by Eisenberg et al. (*Nature* 343:341, 1990), Hannum et al. (*Nature* 343:336, 1990), and Carter et al. (*Nature* 344:633, 1990), which are hereby incorporated by reference in their entireties. These antagonist proteins bind to IL-1 receptors, but have no IL-1-like activity (e.g., do not transduce a signal or otherwise produce the biological effects that result from binding of IL-1 to a cellular IL-1 receptor). The antagonist proteins compete with IL-1 for binding to endogenous IL-1 receptors, thus inhibiting biological effects mediated by IL-1 in vivo.

DNA Sequences Encoding Recombinant Fusion Proteins

Isolated DNA sequences encoding the above-described fusion proteins are also provided by the present invention. A DNA sequence encoding a fusion protein of the present invention is constructed using recombinant DNA techniques to insert DNA fragments encoding the IL-1R or TNF-R polypeptides into an appropriate expression vector. The 3' end of a DNA fragment encoding TNF-R is ligated (via a peptide linker) to the 5' end of the DNA fragment encoding IL-1R with the reading frames of the sequences in phase to permit translation of the mRNA into a single biologically active fusion protein. Alternatively, the 3' end of a DNA fragment encoding IL-1R may be ligated (via a peptide linker) to the 5' end of the DNA fragment encoding TNF-R, with the reading frames of the sequences in phase to permit translation of the mRNA into a single biologically active fusion protein. An additional sequence encoding TNF-R may be ligated in the same reading frame to produce a sequence encoding a fusion protein comprising two TNF-R polypeptides and one IL-1R polypeptide. The IL-1R-encoding sequence is preferably positioned upstream of the TNF-R-encoding sequence(s). While the fusion protein may comprise two IL-1R polypeptides along with the TNF-R polypeptide(s), one IL-1R is preferred. A single IL-1R provides the desired high affinity IL-1 binding activity without the possible disadvantages of increasing the size of the fusion protein by adding a second IL-1R. Such disadvantages may include increased complexity of vector construction procedures and possible reduction in the level of expression of the desired protein. In another embodiment of the present invention, a DNA sequence encoding TNF-R is ligated to a linker sequence which in turn is ligated to a second TNF-R encoding sequence.

A DNA sequence encoding an N-terminal signal sequence may be retained on the DNA sequence encoding the N-terminal polypeptide, while stop codons, which would prevent read-through to the downstream DNA sequence(s), are eliminated. Conversely, a stop codon required to end translation is generally retained on the DNA sequence encoding the C-terminal polypeptide. DNA encoding a signal sequence is preferably removed from DNA sequences other than those encoding the N-terminal polypeptide.

A DNA sequence encoding a desired peptide linker may be inserted between, and in the same reading frame as, the DNA sequences encoding TNF-R or IL-1R using any suitable conventional technique. For example, a chemically synthesized oligonucleotide encoding the linker and containing appropriate restriction endonuclease cleavage sites may be ligated between the sequences encoding TNF-R or IL-1R. Alternatively, a chemically synthesized DNA sequence may contain a sequence complementary to the 3' terminus (without the stop codon) of either TNF-R or IL-1R followed by a linker-encoding sequence which is followed by a sequence complementary to the 5' terminus of the other of TNF-R and IL-1R. Oligonucleotide directed mutagenesis is then employed to insert the linker-encoding sequence into a vector containing a direct fusion of TNF-R and IL-1R. Another technique employs polymerase chain reactions using primers comprising, in part, single strand segments encoding a peptide linker. PCR-generated DNA fragments encoding two different proteins can be joined through annealing of the complementary single stranded linker-encoding segments present at a terminus of each fragment. Preferred procedures for inserting a linker-encoding DNA segment between TNF-R and IL-1R DNA sequences (or between two TNF-R DNA sequences) are described in examples 11 and 12 below.

DNA sequences encoding TNF-R and IL-1R may be isolated by any suitable conventional procedure, for use in constructing the fusion protein-encoding DNA sequences of the present invention. DNA sequences encoding fusion proteins to be expressed in a microorganism will preferably contain no introns that could prematurely terminate transcription of DNA into mRNA; however, premature termination of transcription may be desirable, for example, where it would result in mutants having advantageous C-terminal truncations, for example, deletion of a transmembrane region to yield a soluble receptor not bound to the cell membrane. Among the suitable procedures for cloning type I and type II IL-1R cDNA are those presented in examples 8 and 9, respectively. TNF-R cDNA may be isolated by procedures that include those described in example 3.

The coding sequence of TNF-R may be obtained by isolating a sequence encoding TNF-R from a recombinant cDNA or genomic DNA library. A cDNA library is preferably constructed by obtaining polyadenylated mRNA from a particular cell line which expresses a mammalian TNF-R, for example, the human fibroblast cell line WI-26 VA4 (ATCC CCL 95.1) and using the mRNA as a template for synthesizing double stranded cDNA. The double stranded cDNA is then packaged into a recombinant vector, which is introduced into a host cell (e.g., an appropriate *E. coli* strain) and propagated. TNF-R sequences contained in the cDNA library can be identified by screening the library with an appropriate nucleic acid probe which is capable of hybridizing with human TNF-R cDNA. Another cloning technique that may be employed is the direct expression procedure described in example 3 below. Alternatively, DNAs encoding TNF-R proteins can be assembled by ligation of synthetic oligonucleotide subunits corresponding to all or part of the sequence of FIG. 2 to provide a complete coding sequence.

Additional cDNA clones can be isolated from cDNA libraries of other mammalian species by cross-species hybridization. For use in hybridization, DNA encoding TNF-R or IL-1R may be covalently labeled with a detectable substance such as a fluorescent group, a radioactive atom or a chemiluminescent group by methods well known to those skilled in the pertinent art.

Like most mammalian genes, mammalian TNF receptors and IL-1 receptors are presumably encoded by multi-exon genes. Alternative mRNA constructs which can be attributed to different mRNA splicing events following transcription, and which share large regions of identity or similarity with the cDNAs disclosed herein such that biologically active TNF-R or IL-1R is encoded thereby, are considered to be useful in preparing the fusion proteins of the present invention.

DNA encoding soluble TNF-R and IL-1R polypeptides may be prepared by any of a number of conventional techniques. A DNA fragment encoding a desired soluble polypeptide may be subcloned into an expression vector. DNA fragments may be produced by restriction endonuclease digestion of a full length cloned DNA sequence, and isolated by electrophoresis on agarose gels. Alternatively, a desired DNA sequence may be chemically synthesized using known techniques. Linkers containing restriction endonuclease cleavage site(s) may be employed to insert the desired DNA fragment into an expression vector, or the fragment may be digested at cleavage sites naturally present therein.

The well known polymerase chain reaction (PCR) procedures also may be employed to isolate a DNA sequence encoding a desired soluble protein fragment. This technique is illustrated in the examples below.

In another approach, enzymatic treatment (using Bal 31 exonuclease) may be employed to delete terminal nucleotides from a DNA fragment to obtain a fragment having a particular desired terminus. Among the commercially available linkers are those that an be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence.

The TNF-R and IL-1R DNA sequences may vary from those presented in SEQ ID NOS: 1, 3, 5 and 7. Due to the known degeneracy of the genetic code, there can be considerable variation in nucleotide sequences encoding the same amino acid sequence, for example. DNA sequences capable of hybridizing to the DNA sequences of SEQ ID NOS: 1, 3, 5 and 7 under moderately stringent conditions (55° C., 5×SSC), and which encode a biologically active TNF-R or IL-1R polypeptide, are also considered to be TNF-R-encoding or IL-1R-encoding DNA sequences, respectively, in the context of the present invention.

Mutations may be deliberately made to the native DNA sequences, e.g. to produce the amino acid substitutions, deletions and insertions described above. Certain of the mutations will not be expressed in the final protein product. For example, nucleotide substitutions may be made to enhance expression, primarily to avoid secondary structure loops in the transcribed mRNA (see EP 75,444, incorporated herein by reference). Other alterations of the nucleotide sequence may be made to provide codons that are more readily translated by the selected host, e.g., the well-known E. coli preference codons for E. coli expression. Silent mutations (changes in the DNA sequence that do not alter the encoded amino acid sequence) also may occur during polymerase chain reactions. In one embodiment of the present invention, nucleotide number 437 of SEQ ID NO: 5 (type I IL-1R) is changed from a T to a C. This silent mutation occurred during a polymerase chain reaction.

Mutations in nucleotide sequences should, of course, preserve the reading frame phase of the coding sequences. The mutations preferably will not create complementary regions that could hybridize to produce secondary mRNA structures such as loops or hairpins which would adversely affect translation of the fusion protein mRNA.

The present invention thus provides inventive DNA sequences encoding the above-described fusion proteins, wherein each TNF-R DNA sequence in the fusion protein DNA sequence is selected from: (a) DNA sequences derived from the coding region of a native mammalian TNF-R gene (e.g., cDNA derived from the coding region of SEQ ID NOS: 1 or 3); (b) DNA sequences capable of hybridization to a DNA sequence of (a) under moderately stringent conditions (50° C., 2×SSC) and which encode biologically active TNF-R and (c) DNA sequences which are degenerate as a result of the genetic code to the DNA sequences defined in (a) or (b) and which encode biologically active TNF-R. The fusion protein DNA sequence likewise may comprise IL-1R encoding DNA sequence(s) selected from: (a) DNA sequences derived from the coding region of a native mammalian IL-1R gene (e.g., cDNA derived from the coding region of SEQ ID NOS: 5 or 7); (b) DNA sequences capable of hybridization to a DNA sequence of (a) under moderately stringent conditions (55° C., 5×SSC) and which encode biologically active IL-1R; and (c) DNA sequences which are degenerate as a result of the genetic code to the DNA sequences defined in (a) or (b) and which encode biologically active IL-1R.

Expression of Recombinant Fusion Proteins

The present invention provides recombinant expression vectors to express DNA encoding the fusion proteins of the present invention. The inventive recombinant expression vectors are replicable DNA constructs which contain a synthetic or cDNA-derived DNA sequence encoding one of the above-described fusion proteins, operably linked to suitable transcriptional or translational regulatory elements. Examples of genetic elements having a regulatory role in gene expression include transcriptional promoters, operators or enhancers, a sequence encoding suitable mRNA ribosomal binding sites, and appropriate transcription and translation initiation and termination sequences. The ability to replicate in a host, usually conferred by an origin of replication, and a selection gene to facilitate recognition of transformants may additionally be incorporated. The regulatory elements employed in the expression vectors are generally derived from mammalian, microbial, viral, or insect genes. Expression vectors derived from retroviruses also may be employed.

DNA regions are operably linked when they are functionally related to each other. A DNA sequence encoding a fusion protein is said to be operably linked to one or more of the above-described regulatory elements when the fusion protein DNA sequence is transcribed, or the resulting mRNA is translated, under the control of the regulatory element(s).

Transformed host cells are cells which have been transformed or transfected with foreign DNA using recombinant DNA techniques. In the context of the present invention, the foreign DNA includes a sequence encoding the inventive fusion protein. Host cells may be transformed for purposes of cloning or amplifying the foreign DNA, or may be transformed with an expression vector for production of the fusion protein under the control of appropriate promoters. Suitable host cells include prokaryotes, yeast, or higher eukaryotic cells. Appropriate cloning and expression vectors for use with bacterial, fungal, yeast, and mammalian cellular hosts are described by Pouwels et al. (*Cloning Vectors: A*

*Laboratory Manual,* Elsevier, N.Y., 1985), the relevant disclosures of which is hereby incorporated by reference. Cell-free translation systems could also be employed to produce fusion protein using RNAs derived from the DNA constructs of the present invention.

Prokaryotes include gram negative or gram positive organisms. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Examples of suitable prokaryotic hosts for transformation include *E. coli,* bacilli such as *Bacillus subtilis, Salmonella typhimurium,* and various species within the genera Pseudomonas, Streptomyces, and Staphylococcus, although others may also be employed as a matter of choice.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance, providing simple means for identifying transformed cells.

Promoters commonly used in recombinant microbial expression vectors include the b-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual,* Cold Spring Harbor Laboratory, p. 412, 1982). A particularly useful bacterial expression system employs the phage $\lambda P_L$ promoter and cI857ts thermoinducible repressor. Plasmid vectors available from the American Type Culture Collection which incorporate derivatives of the $\lambda P_L$ promoter include plasmid pHUB2, resident in *E. coli* strain JMB9 (ATCC 37092) and pPLc28, resident in *E. coli* RR1 (ATCC 53082).

The recombinant fusion protein may also be expressed in yeast hosts, preferably from Saccharomyces species, such as *S. cerevisiae.* Yeast of other genera such as Pichia or Kluyveromyces may also be employed. Yeast vectors will generally contain an origin of replication from the 2 μm yeast plasmid or an autonomously replicating sequence (ARS), a promoter, DNA encoding the fusion protein, sequences for polyadenylation and transcription termination and a selection gene. Preferably, yeast vectors will include an origin of replication and selectable markers permitting transformation of both yeast and *E. coli,* e.g., the ampicillin resistance gene of *E. coli* and the *S. cerevisiae* trp 1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al., (*Nature* 300:724, 1982). Advantageously, a DNA segment encoding a leader sequence functional in yeast is operably linked to the 5' end of the DNA encoding the fusion protein. The encoded leader peptide promotes secretion of the fusion protein from the host cell and is generally cleaved from the fusion protein upon secretion. As one example, the yeast α-factor leader, which directs secretion of heterologous proteins, can be inserted between the promoter and the structural gene to be expressed. See, e.g., Kurjan et al., *Cell* 30:922, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art. An exemplary technique is described by Hinnen et al., *Proc. Natl. Acad. Sci. USA* 75:1929, (1978), selecting for Trp$^+$ transformants in a selective medium consisting of 0.67% yeast nitrogen base, 0.5% casamino acids, 2% glucose, 10 μ/ml adenine and 20 μ/ml uracil. Host strains transformed by vectors comprising the above-described ADH2 promoter may be grown for expression in a rich medium consisting of 1% yeast extract, 2% peptone, and 1% glucose supplemented with 80 μ/ml adenine and 80 μ/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Established cell lines of mammalian origin may be employed. Examples of suitable mammalian host cell lines include the COS-7 lines of monkey kidney cells, described by Gluzman (*Cell* 23:175, 1981), L cells, C127, 3T3, Chinese hamster ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin or replication (Fiers et al., *Nature* 273:113, 1978). Smaller or larger SV40 fragments may also be used, provided the approximately 250 bp sequence extending from the Hind III site toward the BglI site located in the viral origin of replication is included. Exemplary vectors can be constructed as disclosed by Okayama and Berg (*Mol. Cell. Biol.* 3:280, 1983). A useful system for stable high level expression of mammalian receptor cDNAs in C127 murine mammary epithelial cells can be constructed substantially as described by Cosman et al. (*Mol. Immunol.* 23:935, 1986).

Producing and Purifying the Fusion Protein

The present invention provides a process for producing the recombinant fusion protein of the present invention, comprising culturing a host cell transformed with an expression vector comprising a DNA sequence that encodes said fusion protein under conditions that promote expression of the fusion protein, which is then purified from culture media or cell extracts. Any suitable purification process may be employed, with the procedure of choice varying according to such factors as the type of host cells and whether or not the desired protein is secreted from the host cells. The fusion protein will be secreted into the culture medium when it is initially fused to a signal sequence or leader peptide operative in the host cells, or when the protein comprises soluble forms of the TNF-R and IL-1R polypeptides.

For example, supernatants from expression systems which secrete recombinant protein into the culture medium can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise TNF or IL-1. An affinity matrix may be prepared by coupling recombinant human TNF or IL-1 to cyanogen bromide-activated Sepharose (Pharmacia) or Hydrazide Affigel (Biorad), according to manufacturer's recommendations. A preferred purification procedure involves sequential immunopurification using antibodies bound to a suitable support. Proteins binding to an antibody specific for TNF-R are recovered and contacted with antibody specific for IL-1R on an insoluble support. Proteins immunoreactive with both antibodies may thus be identified and isolated. A monoclonal antibody specific for human type I IL-1R was deposited with the American Type Culture Collection under accession number HB10556 on Sep. 13, 1990. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. One or more reversed-phase high performance liquid chromatography (RP-HPLC) steps employing hydrophobic RP-HPLC media, e.g., silica gel having pendant methyl or other aliphatic groups, can be employed to further purify a fusion protein composition.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can disrupted by any convenient method, including freeze-thaw cycling, sonication, mechanical disruption, or use of cell lysing agents.

Fermentation of yeast which express fusion proteins as a secreted protein greatly simplifies purification. Secreted recombinant protein resulting from a large-scale fermentation can be purified by methods analogous to those disclosed by Urdal et al. (*J. Chromatog.* 296:171, 1984), involving two sequential, reversed-phase HPLC steps for purification of a recombinant protein on a preparative HPLC column.

Some or all of the foregoing purification steps, in various combinations, can be employed to provide an essentially homogeneous recombinant protein. Recombinant cell culture enables the production of the fusion protein free of those contaminating proteins which may be normally associated with TNF-R or IL-1R as they are found in nature in their respective species of origin, e.g., in cells, cell exudates or body fluids. The foregoing purification procedures are among those that may be employed to purify non-recombinant receptors of the present invention as well.

As an alternative to production of the inventive receptors as fusion proteins, the TNF-R and IL-1R proteins may be separately produced and purified, and subsequently linked together. Numerous reagents useful for crosslinking one protein molecule to another are known. Heterobifunctional and homobifunctional linkers are available for this purpose from Pierce Chemical Company, Rockford, Ill., for example. Such linkers contain two functional groups (e.g., esters and/or maleimides) that will react with certain functional groups on amino acid side chains (e.g., amines on lysine residues and sulfhydryls generated on cysteine residues by reduction), thus linking one polypeptide to another. Examples of such crosslinking reagents are N-maleimidobenzoyl succinimidyl ester and N-hydroxysuccinimide. The reagent and reaction conditions should be chosen such that the cross-linking does not interfere with binding of TNR or IL-1 to the receptor. The TNF-R and IL-1R polypeptides are preferably linked via one of the above-described peptide linkers that functions as a spacer. A peptide linker may be attached to TNF-R or to IL-1R by any of the conventional procedures used to attach one polypeptide to another. The cross-linking reagents available from Pierce Chemical Company as described above are among those that may be employed. Amino acids having side chains reactive with such reagents may be included in the peptide linker, e.g., at the termini thereof.

Pharmaceutical Compositions

The present invention provides pharmaceutical compositions comprising any of the above-described fusion proteins and a physiologically acceptable carrier, diluent, or excipient. Such carriers, excipients and diluents will be nontoxic to recipients at the dosages and concentrations employed. Such compositions may comprise buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, the composition is formulated as a lyophilizate using appropriate excipient solutions (e.g., sucrose) as diluents. Appropriate dosages can be determined in clinical trials. The amount and frequency of administration will depend, of course, on such factors as the nature and severity of the indication being treated, the desired response, the condition of the patient, and so forth.

Conditions mediated by either TNF or IL-1 may be treated by administering a therapeutically effective amount of a fusion protein of the present invention in the form of a pharmaceutical composition, to a patient afflicted with such a disorder. A disorder is said to be mediated by TNF or IL-1 when TNF or IL-1 causes (directly or indirectly) or exacerbates the disorder. Soluble receptor proteins can be used to competitively bind to TNF or IL-1, thereby inhibiting binding of TNF and IL-1 to cell surface receptors.

For therapeutic use, purified fusion proteins of the present invention are administered to a patient, preferably a human, for treatment in a manner appropriate to the indication. Thus, for example, the pharmaceutical compositions can be administered by bolus injection, continuous infusion, sustained release from implants, or other suitable technique.

The fusion protein employed in the pharmaceutical compositions should be purified, in that the fusion protein is substantially free of other proteins of natural or endogenous origin and contains less than about 1% by mass of protein contaminants residual of production processes. Such compositions, however, can contain other proteins added as stabilizers, carriers, excipients or co-therapeutics. The fusion protein is purified to substantial homogeneity if it is detectable as a single protein band in a polyacrylamide gel by silver staining.

The fusion proteins of the present invention may be administered to treat conditions believed to be mediated, at least in part, by TNF, such as cachexia, rheumatoid arthritis, diabetes, multiple sclerosis, pulmonary fibrosis and silicosis, cerebral malaria, and allograft and xenograft rejection in graft versus host disease. TNF has also been implicated in sepsis and septic shock. Bacterial endotoxin can cause sepsis in mammals infected with certain types of bacteria, and is believed to stimulate macrophages to produce factors that include TNF. Folks et al. (*PNAS USA* 86:2365, 1989) suggests that TNF-α plays an important role in the pathogenesis of HIV infection. TNF-α induced expression of HIV in a cell line employed as a model of HIV latency to study conversion from a latent to a productive infection.

Certain cytokines (IL-1, IL-2 and other colony stimulating factors) can induce significant host production of TNF. Fusion proteins of the formula TNF-R-linker-TNF-R thus may be used to treat side effects associated with cytokine therapy. Because of the primary role IL-1 plays in the production of TNF, fusion proteins comprising both IL-1 receptor(s) and TNF receptor(s) may be preferred in the treatment of TNF-associated clinical indications.

TNF has been reported to induce secretion of IL-1 in vivo. Thus, fusion proteins that bind both TNF and IL-1 may be employed in treating conditions mediated by IL-1. The inventive fusion proteins can be administered, for example, for the purpose of suppressing immune responses in a human. A variety of diseases or conditions are caused by an immune response to alloantigen. In alloantigen-induced immune responses, IL-1R suppresses lymphoproliferation and inflammation which result upon activation of T cells. IL-1R thus may be used to suppress alloantigen-induced immune responses in the clinical treatment of, for example, rejection of allografts (such as skin, kidney, and heart transplants), and graft-versus-host reactions in patients who have received bone marrow transplants. IL-1 is believed to play a causative role in allergies and autoimmune dysfunctions (such as rheumatoid arthritis, diabetes, and multiple sclerosis, which are dependent upon the activation of T cells against antigens not recognized as being indigenous to the host.

TNF and IL-1 have been implicated in a number of the same diseases, as can be seen by comparing the lists of TNF-mediated and IL-1-mediated conditions presented above. In addition, TNF and IL-1 are two of the major mediators of inflammation, often acting in concert. The fusion proteins of the present invention that comprise receptors for both TNF and IL-1 thus offer advantages in the treatment of a number of conditions in which both TNF and IL-1 are believed to play a causative role.

The use of soluble forms of IL-1R and TNF-R in the inventive fusion proteins is advantageous for certain applications. Purification of the proteins from recombinant host cells is facilitated, since the soluble proteins are secreted from the cells. Further, soluble proteins are generally more suitable for intravenous administration and may exert their therapeutic effect (binding IL-1 and/or TNF) in the bloodstream. By binding IL-1 and/or TNF, the soluble fusion proteins will inhibit signal transduction via endogenous cell surface receptors for IL-1 or TNF.

The inventive fusion proteins may also be used as reagents in receptor-based immunoassays, reagents in assays for TNF or IL-1, or as binding agents for affinity purification or TNF or IL-1.

The following examples are offered by way of illustration, and not by way of limitation.

EXAMPLES

Example 1

TNF Binding Assays

A. Radiolabeling of TNFα and TNFβ

Recombinant human TNFα in the form of a fusion protein containing a hydrophilic octapeptide at the N-terminus, was expressed in yeast as a secreted protein and purified by affinity chromatography (Hopp et al., *Bio/Technology* 6:1204, 1988). Purified recombinant human TNFβ was purchased from R&D Systems (Minneapolis, Minn.). Both proteins were radiolabeled using the commercially available solid phase agent, IODO-GEN (Pierce). In this procedure, 5 µg of IODO-GEN were plated at the bottom of a 10×75 mm glass tube and incubated for 20 minutes at 4° C. with 75 µl of 0.1 M sodium phosphate, pH 7.4 and 20 µl (2 mCi) Na $^{125}$I. This solution was then transferred to a second glass tube containing 5 µg TNFα (or TNFβ) in 45 µl PBS for 20 minutes at 4° C. The reaction mixture was fractionated by gel filtration on a 2 ml bed volume of Sephadex G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-TNF was diluted to a working stock solution of 1×10$^{-7}$ M in binding medium and stored for up to one month at 4° C. without detectable loss of receptor binding activity. The specific activity is routinely 1×10$^6$ cpm/mmole TNF.

B. Binding to Intact Cells

Binding assays with intact cells were performed by two methods. In the first method, cells were first grown either in suspension (e.g., U 937) or by adherence on tissue culture plates (e.g., WI26-VA4, COS cells expressing the recombinant TNF receptor). Adherent cells were subsequently removed by treatment with 5 mM EDTA treatment for ten minutes at 37 degrees centigrade. Binding assays were then performed by a pthalate oil separation method (Dower et al., *J. Immunol.* 132:751, 1984) essentially as described by Park et al. (*J. Biol. Chem.* 261:4177, 1986). Non-specific binding of $^{125}$I-TNF was measured in the presence of a 200-fold or greater molar excess of unlabeled TNF. Sodium azide (0.2%) was included in a binding assay to inhibit internalization of $^{125}$I-TNF by cells. In the second method, COS cells transfected with the TNF-R-containing plasmid, and expressing TNF receptors on the surface, were tested for the ability to bind $^{125}$I-TNF by the plate binding assay described by Sims et al. (*Science* 241:585, 1988).

C. Solid Phase Binding Assays

The ability of TNF-R to be stably adsorbed to nitrocellulose from detergent extracts of human cells yet retain TNF-binding activity provided a means of detecting TNF-R. Cell extracts were prepared by mixing a cell pellet with a 2×volume of PBS containing 1% Triton X-100 and a cocktail of protease inhibitors (2 mM phenylmethyl sulfonyl fluoride, 10 $\mu$M pepstatin, 10 $\mu$M leupeptin, 2 mM o-phenanthroline and 2 mM EGTA) by vigorous vortexing. The mixture was incubated on ice for 30 minutes after which it was centrifuged at 12,000×g for 15 minutes at 8° C. to remove nuclei and other debris. Two microliter aliquots of cell extracts were placed on dry BA85/21 nitrocellulose membranes (Schleicher and Schuell, Keene, N.H.) and allowed to dry. The membranes were incubated in tissue culture dishes for 30 minutes in Tris (0.05 M) buffered saline (0.15 M) pH 7.5 containing 3% w/v BSA to block nonspecific binding sites. The membrane was then covered with $5 \times 10^{-11}$ M $^{125}$I-TNF in PBS+3% BSA and incubated for 2 hr at 4° C. with shaking. At the end of this time, the membranes were washed 3 times in PBS, dried and placed on Kodak X-Omat AR film for 18 hr at –70° C.

D. Signal Transduction Assays

Inhibition of TNF signal transduction activity can be determined by transfecting cells with recombinant TNF-R DNAs encoding membrane-bound TNF-R to obtain recombinant receptor expression on the cell surface. The cells are then contacted with TNF and the resulting metabolic effects examined. If an effect results which is attributable to the action of the ligand, and is not attributable to endogenous TNF receptors on the cells, then the recombinant receptor has signal transduction activity. Exemplary procedures for determining whether a polypeptide has signal transduction activity are disclosed by Idzerda et al., *J. Exp. Med.* 171:861 (1990); Curtis et al., *Proc. Natl. Acad. Sci. USA* 86:3045 (1989); Prywes et al., *EMBO J.* 5:2179 (1986) and Chou et al., *J. Biol. Chem.* 262:1842 (1987). The ability of a soluble TNF-R polypeptide to competitively inhibit signal transduction can be determined using similar procedures. Primary cells or cell lines which express an endogenous TNF receptor and have a detectable biological response to TNF could be utilized as an alternative to the cells expressing recombinant membrane-bound TNF-R. Decreased signal transduction when a soluble TNF-R polypeptide is added to the assay indicates binding of TNF by the soluble TNF-R, so that less TNF binds to the cell surface TNF receptors to initiate signal transduction.

Example 2

IL-1 Binding Assays

A. Radiolabeling of rIL-1β

Recombinant human IL-1β was prepared by expression in *E. coli* and purification to homogeneity as described by Kronheim et al. (*Bio/Technology* 4:1078, 1986). The IL-1β was labeled with di-iodo ($^{125}$I) Bolton-Hunter reagent (New England Nuclear, Glenolden, Pa.). Ten micrograms (0.57 nmol) of protein in 10 uL of phosphate (0.015 mol/L)-buffered saline (PBS; 0.15 mol/L), pH 7.2, was mixed with 10 uL of sodium borate (0.1 mol/L)-buffered saline (0.15 mol/L), pH 8.5, and reacted with 1 mCi (0.23 nmol) of Bolton-Hunter reagent according to the manufacturer's instructions for 12 hours at 8° C. Subsequently, 30 uL of 2% gelatin and 5 uL of 1 mol/L glycine ethyl ester were added, and the protein was separated from unreacted Bolton-Hunter reagent on a 1 mL bed volume Biogel™ P6 column (BioRad Laboratories, Richmond, Calif.). Routinely, 50% to 60% incorporation of label was observed. Radioiodination yielded specific activities in the range of $1 \times 10^{15}$ to $5 \times 10^{15}$ cpm/mmol-1 (0.4 to 2 atoms I per molecule protein), and sodium dodecyl sulfate-polyacrylamide gel electrophoresis (SDS/PAGE) revealed a single labeled polypeptide of 17.5 kD, consistent with previously reported values for IL-1. The labeled protein was greater than 98% TCA precipitable, indicating that the $^{125}$I was covalently bound to protein.

B. Inhibition Binding Assay for Membrane-Bound IL-1R

"IL-1" refers collectively to IL-1α and IL-1β. The binding inhibition constant of an IL-1R protein may be determined by inhibition binding assays in which varying concentrations of a competitor (IL-1β or IL-1α) are incubated with a constant amount of radiolabeled IL-1β or IL-1α and cells expressing the IL-1R. The non-radiolabeled competitor binds to the receptor and prevents the radiolabeled ligand from binding to the receptor. Binding assays were performed by a phthalate oil separation method essentially as described by Dower et al., *J. Immunol.* 132:751, 1984 and Park et al., *J. Biol. Chem.* 261:4177, 1986. Briefly, host cells expressing a membrane-bound recombinant IL-1R were incubated in six-well plates (Costar, Cambridge, Mass.) at 4° C. for 2 hours with $^{125}$I-IL-1β in 1 ml binding medium (Roswell Park Memorial Institute (RPMI) 1640 medium combining 2% BSA, 20 mM hepes buffer, and 0.1% sodium azide, pH 7.2). Sodium azide was included to inhibit internalization and degradation of $^{125}$I-IL-1 by cells at 37° C. The plates were incubated on a gyratory shaker for 1 hour at 37° C. Replicate aliquots of the incubation mixture were then transferred to polyethylene centrifuge tubes containing a phthalate oil mixture comprising 1.5 parts dibutylphthalate, to 1 part bis(s-ethylhexyl)phthalate. Control tubes containing a 100×molar excess of unlabeled IL-18 were also included to determine non-specific binding. The cells with bound $^{125}$I-IL-1 were separated from unbound $^{125}$I-IL-1 by centrifugation for 5 minutes at 15,000×g in an Eppendorf Microfuge. The radioactivity associated with the cells was then determined on a gamma counter.

C. Inhibition Binding Assay for Soluble IL-1R

The binding inhibition constant of a soluble human IL-1R may be determined by an inhibition binding assay in which varying concentrations of an IL-1β competitor is incubated with a constant amounts of radiolabeled I-IL-1β and CB23 cells (an Epstein Barr virus transformed cord blood B lymphocyte cell line) expressing the type II IL-1R. A cell line expressing endogenous type I IL-1 receptors may be substituted for the CB23 cells in assays involving soluble type I IL-1R. Binding assays were performed by a phthalate oil separation method essentially as described by Dower et al., *J. Immunol.* 132:751, 1984 and Park et al., *J. Biol. Chem.* 261:4177, 1986. Briefly, CVI-EBNA (mammalian) cells were transfected with the expression vector pDC406 containing a cDNA encoding a soluble human type II IL-1R as described in example 10. Supernatants from the cells were harvested 3 days after transfection and serially diluted in binding medium (Roswell Park Memorial Institute (RPMI) 1640 medium containing 2% BSA, 20 mM Hepes buffer, and 0.2% sodium azide, pH 7.2) in 6 well plates to a volume of 50 $\mu$l/well. The supernatants were incubated with 50 $\mu$l of $9 \times 10^{-10}$ M $^{125}$I-IL-1β plus $2.5 \times 10^6$ CVI-EBNA cells at 8° C. for 2 hours with agitation. Duplicate 60 $\mu$l aliquots of the incubation mixture were then transferred to polyethylene centrifuge types containing a phthalate oil mixture comprising 1.5 parts dibutylphthalate, to 1 part bis(s-ethylhexyl) phthalate. A negative control tube containing $3\times10^{-6}$ M unlabeled IL-1β was also included to determine non-specific binding (100% inhibition) and a positive control tube containing 50 ml binding medium with only radiolabeled IL-1 was included to determine maximum binding. The cells with bound $^{125}$I-IL-1β were separated from unbound $^{125}$I-IL-1β by centrifugation for 5 minutes at 15,000×g in an Eppendorf Microfuge. Supernatants containing unbound $^{125}$I-IL-1β were discarded and the cells were carefully rinsed with ice-cold binding medium. The cells were incubated in 1 ml of trypsin-EDTA at 37° C. for 15 minutes and then harvested. The radioactivity associated with the cells was then determined on a gamma counter. The ability of soluble IL-1β to inhibit binding of IL-1α to endogenous cellular receptors may be determined by the same procedure. Analogous techniques may be employed in assays involving soluble TNF-R.

Example 3

Isolation of Human TNF-R cDNA by Direct Expression of Active Protein in COS-7 Cells Various human cell lines were screened for expression of TNF-R based on their ability to bind $^{125}$I-labeled TNF. The human fibroblast cell line WI-26 VA4 (ATCC CCL 95.1) was found to express a reasonable number of receptors per cell. Equilibrium binding studies showed that the cell line exhibited biphasic binding of $^{125}$I-TNF with approximately 4,000 high affinity sites ($K_a=1\times10^{10}$ $M^{-1}$) and 15,000 low affinity sites ($K_a=1\times10^{8}$ $M^{-1}$) per cell.

An unsized cDNA library was constructed by reverse transcription of polyadenylated mRNA isolated from total RNA extracted from human fibroblast WI-26 VA4 cells grown in the presence of pokeweed mitogen using standard techniques (Gubler, et al., *Gene* 25:263, 1983; Ausubel et al., eds., *Current Protocols in Molecular Biology, Vol.* 1, 1987). The cells were harvested by lysing the cells in a guanidine hydrochloride solution and total RNA isolated as previously described (March et al., *Nature* 315:641, 1985).

Poly A$^+$ RNA was isolated by oligo dT cellulose chromatography and double-stranded cDNA was prepared by a method similar to that of Gubler and Hoffman (*Gene* 25:263, 1983). Briefly, the poly A$^+$ RNA was converted to an RNA-cDNA hybrid by reverse transcriptase using oligo dT as a primer. The RNA-cDNA hybrid was then converted into double-stranded cDNA using RNAase H in combination with DNA polymerase I. The resulting double stranded cDNA was blunt-ended with T4 DNA polymerase. To the blunt-ended cDNA is added EcoRI linker-adapters (having internal Not1 sites) which were phosphorylated on only one end (Invitrogen). The linker-adaptered cDNA was treated with T4 polynucleotide kinase to phosphorylate the 5' overhanging region of the linker-adapter and unligated linkers were removed by running the cDNA over a Sepharose CL4B column. The linker-adaptered cDNA was ligated to an equimolar concentration of EcoR1 cut and dephosphorylated arms of bacteriophage λgt10 (Huynh et al, *DNA Cloning: A Practical Approach,* Glover, ed., IRL Press, pp. 49–78). The ligated DNA was packaged into phage particles using a commercially available kit to generate a library of recombinants (Stratagene Cloning Systems, San Diego, Calif., USA). Recombinants were further amplified by plating phage on a bacterial lawn of *E. coli* strain c600(hfl$^-$).

Phage DNA was purified from the resulting λgt10 cDNA library and the cDNA inserts excised by digestion with the restriction enzyme Not1. Following electrophoresis of the digest through an agarose gel, cDNAs greater than 2,000 bp were isolated.

The resulting cDNAs were ligated into the eukaryotic expression vector pCAV/NOT, which was designed to express cDNA sequences inserted at its multiple cloning site when transfected into mammalian cells. pCAV/NOT was assembled from pDC201 (a derivative of pMLSV, previously described by Cosman et al., *Nature* 312: 768, 1984),. SV40 and cytomegalovirus DNA and comprises, in sequence with the direction of transcription from the origin of replication: (1) SV40 sequences from coordinates 5171–270 including the origin of replication, enhancer sequences and early and late promoters; (2) cytomegalovirus sequences including the promoter and enhancer regions (nucleotides 671 to +63 from the sequence published by Boechart et al. (*Cell* 41:521, 1985); (3) adenovirus-2 sequences containing the first exon and part of the intron between the first and second exons of the tripartite leader, the second exon and part of the third exon of the tripartite leader and a multiple cloning site (MCS) containing sites for Xho1, Kpn1, Sma1, Not1 and Bgl1; (4) SV40 sequences from coordinates 4127–4100 and 2770–2533 that include the polyadenylation and termination signals for early transcription; (5) sequences derived from pBR322 and virus-associated sequences VAI and VAII of pDC201, with adenovirus sequences 10532–11156 containing the VAI and VAII genes, followed by pBR322 sequences from 4363–2486 and 1094–375 containing the ampicillin resistance gene and origin of replication. pCAV/NOT has been deposited with the American Type Culture Collection under accession no. ATCC 68014.

The resulting WI-26 VA4 cDNA library in pCAV/NOT was used to transform *E. coli* strain DH5α and recombinants were plated to provide approximately 800 colonies per plate and sufficient plates to provide approximately 50,000 total colonies per screen. Colonies were scraped from each plate, pooled, and plasmid DNA prepared from each pool. The pooled DNA was then used to transfect a sub-confluent layer of monkey COS-7 cells using DEAE-dextran followed by chloroquine treatment, as described by Luthman et al. (*Nucl. Acids Res.* 11:1295, 1983) and McCutchan et al. (*J. Natl. Cancer Inst.* 41:351, 1986). The cells were then grown in culture for three days to permit transient expression of the inserted sequences. After three days, cell culture supernatants were discarded and the cell monolayers in each plate assayed for TNF binding as follows. Three ml of binding medium containing $1.2\times10^{-11}$ M $^{125}$I-labeled FLAG®-TNF was added to each plate and the plates incubated at 4° C. for 120 minutes. This medium was then discarded, and each plate was washed once with cold binding medium (containing no labeled TNF) and twice with cold PBS. The edges of each plate were then broken off, leaving a flat disk which was contacted with X-ray film for 72 hours at −70° C. using an intensifying screen as described by Sims et al., *Science* 241:585 (1988). TNF binding activity was visualized on the exposed films as a dark focus against a relatively uniform background.

After approximately 240,000 recombinants from the library had been screened in this manner, one transfectant pool was observed to provide TNF binding foci which were clearly apparent against the background exposure. A frozen stock of bacteria from the positive pool was then used to obtain plates of approximately 150 colonies. Replicas of these plates were made on nitrocellulose filters, and the plates were then scraped and plasmid DNA prepared and transfected as described above to identify a positive plate. Bacteria from individual colonies from the nitrocellulose replica of this plate were grown in 0.2 ml cultures, which were used to obtain plasmid DNA, which was transfected into COS-7 cells as described above. In this manner, a single clone was isolated which was capable of inducing expression of human TNF-R in COS cells. The expression vector pCAV/NOT containing this TNF-R cDNA has been deposited with the American Type Culture Collection, 12301 Parklawn Drive, Rockville, Md. 20852, USA (Accession No. 68088) under the name pCAV/NOT-TNF-R.

Example 4

Construction of cDNAs Encoding Soluble huTNF-RΔ235

A cDNA encoding a soluble huTNF-RΔ235 was constructed. The encoded protein comprises the sequence of amino acids −22 to 235 of FIG. 2. Processing of the signal sequence yields a protein having the sequence of amino acids 1 to 235 of FIG. 2. An 840 bp fragment was excised from pCAV/NOT-TNF-R with the restriction enzymes Not1 and Pvu2. Not1 cuts at the multiple cloning site of pCAV/NOT-TNF-R and Pvu2 cuts within the TNF-R coding region 20 nucleotides 5' of the transmembrane region. In order to reconstruct the 3' end of the TNF-R sequences, two oligonucleotides were synthesized and annealed to create the following oligonucleotide linker:

```
  Pvu2                    BamH1 Bgl2   SEQ ID NO: 9
CTGAAGGGAGCACTGGCGACTAAGGATCCA

GACTTCCCTCGTGACCGCTGATTCCTAGGTCTAG
AlaGluGlySerThrGlyAspEnd
```

This oligonucleotide linker has terminal Pvu2 and Bgl2 restriction sites, regenerates 20 nucleotides of the TNF-R, followed by a termination codon (underlined) and a BamH1 restriction site (for convenience in isolating the entire soluble TNF-R by Not1/BamH1 digestion). This oligonucleotide was then ligated with the 840 bp Not1/Pvu2 TNF-R insert into Bgl2/Not1 cut pCAV/NOT to yield psolhuTNF-RΔ235/CAVNOT, which was transfected into COS-7 cells as described above. This expression vector induced expression of soluble human TNF-R which was capable of binding TNF.

Example 5

Construction of cDNAs Encoding Soluble huTNF-RΔ185

A cDNA encoding a soluble huTNF-RΔ185 having the sequence of amino acids −22−185 of FIG. 2 (or amino acids 1−185 upon processing of the signal sequence in an appropriate host cell) was constructed by excising a 640 bp fragment from pCAV/NOT-TNF-R with the restriction enzymes Not1 and Bgl2. Not1 cuts at the multiple cloning site of pCAV/NOT-TNF-R and Bgl2 cuts within the TNF-R coding region at nucleotide 637, which is 237 nucleotides 5' of the transmembrane region. The following oligonucleotide linkers were synthesized:

The above oligonucleotide linkers reconstruct the 3' end of the receptor molecule up to nucleotide 708, followed by a termination codon (underlined). These oligonucleotides were then ligated with the 640 bp Not1 TNF-R insert into Not1 cut pCAV/NOT to yield the expression vector psolTNFRΔ185/CAVNOT, which was transfected into COS-7 cells as described above. This expression vector induced expression of soluble human TNF-R which was capable of binding TNF.

Example 6

Construction of cDNAs Encoding Soluble huTNF-RΔ163

A cDNA encoding a soluble huTNF-RΔ163 having the sequence of amino acids −22−163 of FIG. 2 (1−163 upon processing of the signal sequence) was constructed by excising a 640 bp fragment from from pCAV/NOT-TNF-R with the restriction enzymes Not1 and Bgl2 as described in Example 4. The following oligonucleotide linkers were synthesized:

```
     Bgl2         Not1           SEQ ID NO: 12
   5'-GATCTGTTGAGC          -3'
          ACAACTCGCCGG
          IleCysEnd
```

This above oligonucleotide linker reconstructs the 3' end of the receptor molecule up to nucleotide 642 (amino acid 163), followed by a termination codon (underlined). This oligonucleotide was then ligated with the 640 bp Not1 TNF-R insert into Not1 cut pCAV/NOT to yield the expression vector psolTNFRΔ163/CAVNOT, which was transfected into COS-7 cells as described above. This expression vector induced expression of soluble human TNF-R which was capable of binding TNF in the binding assay described in Example 1.

Example 7

Construction of cDNAs Encoding Soluble huTNF-RΔ142

A cDNA encoding a soluble huTNF-RΔ142 (having the sequence of amino acids −22−142 of FIG. 2 (1−142 upon processing of the signal sequence) was constructed by excising a 550 bp fragment from from pCAV/NOT-TNF-R with the restriction enzymes Not1 and AlwN1. AlwN1 cuts within the TNF-R coding region at nucleotide 549. The following oligonucleotide linker was synthesized:

```
  Bgl2
5'-GATCTGTAACGTGGTGGCCATCCCTGGGAATGCAAGCATGGATGC-3'    SEQ ID NO: 10
       ACATTGCACCACCGGTAGGGACCCTTACGTTCG
       IleCysAsnValValAlaIleProGlyAsnAlaSerMetAspAla

Not1            SEQ ID NO:   11
  5'-    AGTCTGCACGTCCACGTCCCCCACCCGGTGAGC    -3'
TACCTACGTCAGACGTGCAGGTGCAGGGGGTGGGCCACTCGCCGG
         ValCysThrSerThrSerProThrArgEnd
```

```
   Bgl2         NotI
5'-CTGAAACATCAGACGTGGTGTGCAAGCCCTGTTAAA-3'    SEQ ID
   CTTGACTTTGTAGTCTGCACCACACGTTCGGGACAATTTCTAGA NO: 13
                                          End
```

This above oligonucleotide linker reconstructs the 3' end of the receptor molecule up to nucleotide 579 (amino acid 142), followed by a termination codon (underlined). This oligonucleotide was then ligated with the 550 bp NotI/AlwNI TNF-R insert into NotI/Bgl2 cut pCAV/NOT to yield the expression vector psolTNFRΔ142/CAVNOT, which was transfected into COS-7 cells as described above. This expression vector did not induce expression of soluble human TNF-R which was capable of binding TNF. It is believed that this particular construct failed to express biologically active TNF-R because one or more essential cysteine residues (e.g., $Cys^{157}$ or $Cys^{163}$) required for intramolecular bonding (for formation of the proper tertiary structure of the TNF-R molecule) was eliminated.

Example 8

Isolation of Human Type I IL-1R cDNA Clones cDNA encoding a human type I IL-1R protein was isolated by hybridization to a probe derived from murine type I IL-1R cDNA. Cloning of this murine IL-1R cDNA is described in example 4 of EP 318,296. A vector containing the murine cDNA was deposited with the American Type Culture Collection under the name GEMBL78 on Nov. 19, 1987 and given the accession number ATCC 67563.

A 2356 base pair (bp) fragment of this deposited murine clone 78 was isolated as described by Sims et al. (Science 241:585, 1988) and radiolabeled by nick-translation using DNA polymerase I for use as a probe. The method employed was substantially similar to that disclosed by Maniatis et al. (*Molecular Cloning: A Laboratory Manual*, Cold Spring Harbor Laboratory, 1982, p. 109).

The probe was used to screen human cDNA libraries for human IL-1R, as described by Sims et al., *Proc. Natl. Acad. Sci.* (USA) 86:8946, 1989. A cDNA library was constructed by reverse transcription of polyadenylated mRNA isolated from total RNA extracted from the cultured cells of a human T-cell line designated clone 22, described by Acres et al. (*J. Immunol.* 138:2132, 1987). These cells were cultured in RPMI 1640 medium plus 10% fetal bovine serum as described by Acres et al. (supra), in the presence of 10 ng/ml OKT3 antibody and 10 ng/ml human IL-2. The cDNA was rendered double-stranded using DNA polymerase I, blunt-ended with T4 DNA polymerase, methylated with EcoRI methylase to protect EcoRI cleavage sites within the cDNA, and ligated to EcoRI linkers. The resulting constructs were digested with EcoRI to remove all but one copy of the linkers at each end of the cDNA, and ligated to EcoRI-cut and dephosphorylated arms of bacteriophage λgt10 (Huynh et al., DNA *Cloning: A Practical Approach*, Glover, ed., IRL Press, pp. 49–78). The ligated DNA was packaged into phage particles using a commercially available kit (Stratagene Cloning Systems, San Diego, Calif., USA 92121) to generate a library of recombinants. Recombinants were plated on *E. coli* strain C600(hfl−) and screened by standard plaque hybridization techniques under conditions of moderate stringency (50° C., 6×SSC).

Following several rounds of screening, nine clones were isolated from the library which hybridized to the cDNA probe. The clones were plaque purified and used to prepare bacteriophage DNA which was digested with EcoRI. The digests were electrophoresed on an agarose gel, blotted onto nylon filters, and retested for hybridization. The clones were digested with EcoRI followed by preparative agarose gel electrophoresis, then subcloned into an EcoRI-cut derivative (pGEMBL) of the standard cloning vector pBR322 containing a polylinker having a unique EcoRI site, a BamH1 site and numerous other unique restriction sites. An exemplary vector of this type is described by Dente et al. (*Nucl. Acids Res.* 11:1645, 1983).

Restriction mapping and sequencing of a 4.8 kb human IL-1R clone indicated that the clone included a sequence encoding 518 amino acids which exhibited 80% amino acid sequence identity to the corresponding murine sequence in the extracellular, or N-terminal region distal to the transmembrane region, 63% identity in the transmembrane region, and 87% identity in the cytoplasmic, or C-terminal region. A 440 bp EcoRI-NsiI fragment derived from the 5' portion of the human IL-1R clone was $^{32}$P-labeled by nick-translation as described above and used to screen a cDNA library produced by randomly-priming human T cell line clone 22 mRNA prepared as described above. 23 clones which hybridized to the probe were isolated and analyzed by restriction mapping. Sequencing of one of these clones provided the sequence information corresponding to the remaining N-terminal 34 amino acids of the human protein. The DNA and deduced amino acid sequence of the complete coding region of the type I human IL-1R are shown in SEQ ID NOS: 5 and 6. This human IL-1R protein comprises 569 amino acids (including a 20 amino acid signal peptide), and includes 16 cysteine residues, 13 of which are conserved between the murine and human genes. In addition, the human sequence includes six potential N-glycosylation sites, of which five are conserved between murine and human.

Example 9

Isolation of cDNAs Encoding Type II IL-1R

A DNA sequence encoding human type II IL-1R was isolated from a cDNA library prepared using standard methods, by reverse transcription of polyadenylated RNA isolated from the human B cell lymphoblastoid line CB23, described by Benjamin & Dower, *Blood* 75:2017, 1990. Briefly, the CB23 cell line is an EBV-transformed cord blood (CB) lymphocyte cell line, which was derived using the methods described by Benjamin et al., *Proc. Natl. Acad. Sci. USA* 81:3547, 1984.

The CB23 library was screened by modified direct expression of pooled cDNA fragments in the monkey kidney cell line CV-1/EBNA-1 using a mammalian expression vector (pDC406) that contains origins of replication derived from SV40, Epstein-Barr virus and pBR322. pDC406 is a derivative of HAV-EO described by Dower et al., *J. Immunol.* 142:4314 (1989). pDC406 differs from HAV-EO by the deletion of the intron present in the adenovirus 2 tripartite leader sequence in HAV-EO. The CV-1/EBNA-1 cell line was derived by transfection of the CV-1 cell line with the gene encoding Epstein-Barr virus nuclear antigen-1 (EBNA-1) and with a vector containing CMV regulatory sequences, so that EBNA-1 is expressed under the control of the human CMV immediate-early enhancer/promoter. The EBNA-1 gene allows the episomal replication of expression vectors such as pDC406 that contain the EBV origin of replication.

Transfectants expressing biologically active type II IL-1R were initially identified using a modified slide autoradiographic technique, substantially as described by Gearing et al., *EMBO J.* 8:3667, 1989. Briefly, CV-1/EBNA-1 cells were transfected with miniprep DNA in pDC406 from pools of cDNA clones directly on glass slides and cultured for 2–3 days to permit transient expression of type II IL-1R. The slides containing the transfected cells were then incubated with medium containing $^{125}$I-IL-1β, washed to remove unbound labeled IL-1β, fixed with gluteraldehyde, and dipped in liquid photographic emulsion and exposed in the dark. After developing the slides, they were individually examined with a microscope and positive cells expressing type II IL-1R were identified by the presence of autoradiographic silver grains against a light background.

Using this approach, approximately 250,000 cDNAs were screened in pools of approximately 3,000 cDNAs using the slide autoradiographic method until assay of one transfectant pool showed multiple cells clearly positive for IL-1β binding. This pool was then partitioned into pools of 500 and again screened by slide autoradiography. A positive pool was identified. This pool was further partitioned into pools of 75 and screened by plate binding assays analyzed by quantitation of bound $^{125}$IL-1β. The cells were scraped off and counted to determine which pool of 75 was positive. Individual colonies from this pool of 75 were screened until a single clone was identified which directed synthesis of a surface protein with detectable IL-1β binding activity. This clone was isolated, and its insert was sequenced to determine the sequence of the human type II IL-1R cDNA that is presented along with the amino acid sequence encoded thereby in SEQ ID NOS: 7 and 8. The pDC406 cloning vector containing the human type II IL-1R cDNA, designated pHu IL-1R-II 75, was deposited in *E.coli* host cells with the American Type Culture Collection, Rockville, Md. USA (ATCC) on Jun. 5, 1990 under accession number ATCC 68337. The deposit was made under the conditions of the Budapest Treaty.

Like most mammalian genes, mammalian type II IL-1R is presumably encoded by multi-exon genes. Alternative mRNA constructs which can be attributed to different mRNA splicing events following transcription, and which share large regions of identity or similarity with the cDNAs claimed herein, are considered to be within the scope of the present invention.

Example 10

Construction and Expression of cDNAs Encoding Human Soluble Type II IL-1R

A cDNA encoding a soluble human type II IL-1R (having the sequence of amino acids -13-333 of SEQ ID NO: 8) was constructed by polymerase chain reaction (PCR) amplification using the full length type II IL-1R cDNA clone 75 (ATCC 68337) in vector pDC406 (described in example 9) as a template. The following 5' oligonucleotide primer (SEQ ID NO: 14) and 3' oligonucleotide primer (SEQ ID NO: 15) were first constructed:

```
5'-GCGTCGACCTAGTGACGCTCATACAAATC-3'       SEQ ID NO:
     <SalI>                                      14

5'-GCGCGGCCGCTCAGGAGGAGGCTTCCTTGACTG-3'   SEQ ID NO:
     <-NotI->End\1191            \1172           15
```

The 5' primer corresponds to nucleotides 31–51 from the untranslated region of human type II IL-1R clone 75 (SEQ ID NO:7) with a 5' add-on of a SalI restriction site; this nucleotide sequence is capable of annealing to the (−) strand complementary to nucleotides 31–51 of human clone 75.

The 3' primer is complementary to nucleotides 1191–1172 (which includes anti-sense nucleotides encoding 3 amino acids of human type II IL-1R clone 75 and has a 5' add-on of a NotI restriction site and a stop codon.

The following PCR reagents were added to a 1.5 ml Eppendorf microfuge tube: 10 μl of 10×PCR buffer (500 mM KCl, 100 mM Tris-HCl, pH 8.3 at 25° C., 15 mM MgCl$_2$, and 1 mg/ml gelatin) (Perkins-Elmer Cetus, Norwalk, Conn.), 10 μl of a 2 mM solution containing each dNTP (2 mM dATP, 2 mM dCTP, 2 mM dGTP and 2 mM dTTP), 2.5 units (0.5 μl of standard 5000 units/ml solution) of Taq DNA polymerase (Perkins-Elmer Cetus), 50 ng of template DNA and 5 μl of a 20 μM solution of each of the above oligonucleotide primers and 74.5 μl water to a final volume of 100 μl. The final mixture was then overlaid with 100 μl parafin oil. PCR was carried out using a DNA thermal cycler (Ericomp, San Diego, Calif.) by initially denaturing the template at 94° for 90 seconds, reannealing at 55° for 75 seconds and extending the cDNA at 72° for 150 seconds. PCR was carried out for an additional 20 cycles of amplification using a step program (denaturation at 94°, 25 sec; annealing at 55°, 45 sec; extension at 72°, 150 sec.), followed by a 5 minute extension at 72°.

The sample was removed from the parafin oil and DNA extracted by phenolchloroform extraction and spun column chromatography over G-50 (Boehringer Mannheim). A 10 μl aliquot of the extracted DNA was separated by electrophoresis on 1% SeaKem agarose (FMC BioProducts, Rockland, Me.) and stained with ethidium bromide to confirm that the DNA fragment size was consistent with the predicted product.

20 μl of the PCR-amplified cDNA products were then digested with SalI and NotI restriction enzymes using standard procedures. The SalI/NotI restriction fragment was then separated on a 1.2% Seaplaque™ low gelling temperature (LGT) agarose, and the band representing the fragment was isolated. The fragment was ligated into the pDC406 vector by a standard "in gel" ligation method. The resulting vector was transfected into CV1-EBNA cells and the soluble IL-1R protein was expressed.

Example 11

Construction of Vector Encoding Di-TNF-R

A vector encoding a fusion protein of the formula TNF-R—peptide linker—TNF-R and depicted in FIG. 3 was constructed as follows. Pertinent restriction enzyme cleavage sites in the TNF-R sequence are also shown in FIG. 2.

The expression vector constructed in example 4 and designated psol huTNF-RΔ235/CAVNOT was digested with the restriction enzyme Not I, which cuts at the multiple cloning site of the pCAV/NOT vector (i.e., upstream of the TNF-R sequence inserted therein). The overhang generated by Not I digestion was filled in using the Klenow fragment of DNA polymerase I to produce a blunt end. The vector was then digested with Bam HI which cleaves downstream of the stop codon that follows the codon for amino acid 235, as shown in example 4.

The blunted NotI/Bam HI fragment containing the TNF-R sequence was isolated by conventional procedures and inserted into a plasmid vector designated pCAV/DHFR which had been digested with Sma I and Bgl II. The pCAV/DHFR vector is an expression vector containing SV40 promoter sequences upstream of a multiple cloning site and other features as described for pCAV/NOT in example 3, and also contains a dihydrofolate reductase (DHFR) gene as a selectable marker. The DHFR gene confers a selective advantage on otherwise DHFR⁻ mammalian cells that have taken up the vector, when grown in the presence of methotrexate (MTX). Sma I digestion produces blunt ends, to which the blunted Not I ends of the TNF-R-containing fragment are ligated. The Bgl II-generated overhangs are ligated to the Bam HI-digested ends of the TNF-R-containing fragment. The ligation destroys the Bam HI and Bgl II sites. *E. coli* cells are transformed with the ligation mixture by conventional procedures. Plasmid DNA is recovered from the host cells and the desired construct is confirmed by restriction analysis. The resulting vector containing the TNF-R insert is designated pCAV/DHFR/TNF-R.

The following DNA fragments were isolated for use in preparing a vector encoding two TNF-R polypeptides separated by a peptide linker:

(A) Asp718 (a restriction enzyme) to Esp I fragment of the pCAV/DHFR/TNF-R vector. Asp 718 cleaves the vector upstream of the inserted TNF-R sequence; EspI (available from U.S. Biochemicals) cleaves the TNF-R sequence at the position shown in FIG. 2. The desired fragment is about 6.7 kilobase-pairs (kbp) in length and includes vector sequences and the 3' end of a TNF-R sequence.

(B) Asp718 to PvuII fragment of the expression vector constructed in example 4 and designated psol hu TNF-R Δ235/CAVNOT. Asp718 cleaves the vector upstream of the inserted TNF-R sequence. The desired 865 bp fragment includes a TNF-R sequence extending from the 5' signal sequence through the Pvu II site shown in example 4.

(C) a double-stranded oligonucleotide having the sequence (SEQ ID NOS: 16 and 17):

```
5' CTGAAGGGAGCACTGGCGACGGTGGCG-
   GTGGATCCGGCGGTGGCGGCGGCTCAT-
   TGCCCGCCCAGG 3'

3' GACTTCCCTCGTGACCGCTGCCACCGC-
   CACCTAGGCCGCCACCGCCGCCGAGTAACGGGCGGG 5'

GluGlySerThrGlyAspGlyGlyG-
   lyGlySerGlyGlyGlyGlyGlySerLeuProAlaGlnVal
```

(D) Bgl I to Esp I fragment of the expression vector constructed in example 4 and designated psol hu TNF-R Δ235/CAVNOT. The desired fragment is about 304 bp in length. Bgl I cleaves within the codon for amino acid 5 (Val) of TNF-R; Esp I cleaves the TNF-R sequence at the position shown in FIG. 2; the remainder (3' end) of this soluble TNF-R-encoding sequence is provided by fragment (A).

The oligonucleotide (C) is prepared by conventional procedures for chemical synthesis of oligonucleotides. The oligonucleotide reconstructs the 3' end of the first TNF-R sequence from the Pvu II site through the last amino acid of the extracellular domain (Asp at position 235). The oligonucleotide also contains an in-frame sequence encoding the peptide linker Gly$_4$SerGly$_5$Ser (SEQ ID NO:23). The sequence of this portion of the oligonucleotide may be varied if desired to encode other peptide linkers. Oligonucleotide C also reconstructs the 5' end of the second TNF-R sequence from a codon for leucine, the first amino acid of the mature protein, through a partial codon for valine (amino acid 5) within the protruding 3' overhang, which will regenerate the Val codon when ligated to the complementary overhang on the Bgl I-digested end of fragment D.

Figure 3:
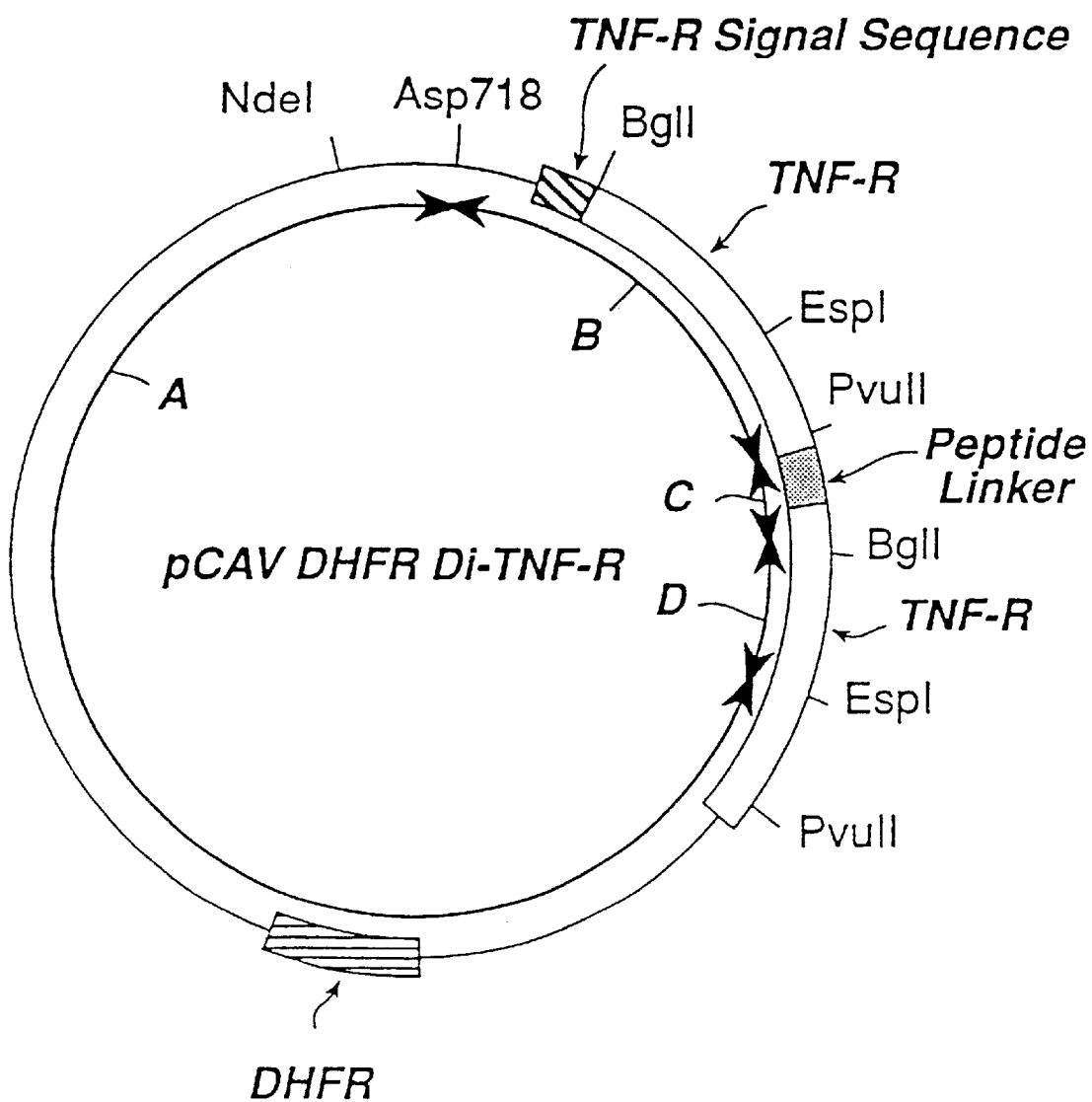
FIG. 3 depicts a plasmid vector comprising a DNA fragment encoding a fusion protein of the formula TNF-R-linker-TNF-R, constructed as described in example 11.

The DNA fragments designated A–D were ligated together in the positions shown in FIG. 3 to form a vector designated pCAV DHFR Di-TNF-R which encodes a fusion protein of the present invention. *E. coli* cells are transformed with the ligation mixture by conventional procedures. Plasmid DNA is recovered from the host cells and the desired construct is confirmed by restriction analysis. The upstream TNF-R polypeptide encoded by this expression vector contains amino acids –22 to 235 of SEQ ID NO:2 (i.e., a soluble TNF-R including the N-terminal signal sequence and the entire extracellular domain without a stop codon). The downstream TNF-R polypeptide lacks the signal sequence and contains amino acids 1–235 of SEQ ID NO:2, with a stop codon positioned immediately after amino acid 235. The peptide linker of this particular construct is Gly$_4$SerGly$_5$Ser (SEQ ID NO:23).

Mammalian cells are transfected with the expression vector by conventional procedures and cultured to produce the desired fusion protein. One suitable mammalian cell line is a DHFR⁻ Chinese hamster ovary cell line designated CHO-K1 and available from the American Type Culture Collection, Rockville, Md., under accession number CCL61. The cells may be transfected with the expression vector by standard calcium phosphate precipitation, essentially as described by Graham and van der Eb, *Virology* 52:456 (1983). The transfected cells are cultured under suitable conventional conditions, and the presence of the desired fusion protein in the culture medium is confirmed by assays such as those described in examples 1 and 2.

Example 12

Fusion Protein Comprising One IL-1R Polypeptide and Two TNF-R Polypeptides

A plasmid vector containing DNA encoding a fusion protein of the formula IL-1R-peptide linker-TNF-R-peptide linker-TNF-R is constructed as follows.

cDNA encoding a soluble type I IL-1R polypeptide was isolated and amplified using the well known polymerase chain reaction (PCR) procedure. The following oligonucleotides were synthesized for use as primers in the PCR reaction:

5' ACCGAGGGACCTGAGCG 3'          SEQ ID NO: 18

3' TCAATTATATAGGTCAGTGACCACCGC-
   CACCTAGGCCGCCACCGCCGCCGAGT 5'  SEQ ID NO: 19

These oligonucleotides as well as those discussed below are synthesized by conventional procedures, e.g., by using an automated DNA synthesis machine such as those available from Biosearch, Inc., San Rafael, Calif. or Applied Biosystems. The template employed in the PCR reaction is a plasmid vector prepared by inserting type I human IL-1R cDNA into a vector designated SF CAV. The SF CAV vector is a mammalian expression vector shown in FIG. 5 (which depicts the use of SF CAV in an additional vector construction described below.) SF CAV in *E. coli* cells was deposited with the American Type Culture Collection on Feb. 27, 1992, under the terms of the Budapest Treaty, and was given accession number 68922.

The SV40, CMV, pA, and VA sequences and ampicillin resistance gene in SF CAV are as described for pCAV/NOT in example 3 above and also in example 8 and FIG. 3 of PCT application WO 90/05183. A multiple cloning site positioned between the adenovirus-2 tripartite leader (TPL) and pA sequences contains recognition sites for the restriction endonucleases XhoI, KpnI, SmaI, NotI, and BglI. The TPL sequence differs from that of pCAV/NOT in that a region believed to be detrimental to construction of IL-1R-encoding vectors has been deleted from the SF CAV TPL sequence. The adverse impact on IL-1R vectors may possibly be attributable to a cryptic promoter in the undesirable sequence, from which undesired protein is expressed in *E. coli*. Low level expression of human IL-1R off the cryptic promoter may be toxic to the bacteria.

SF CAV is digested with SmaI, which recognizes a unique restriction site within the multiple cloning site and produces blunt ends. A DNA fragment containing type I IL-1R cDNA is produced by StyI/BglII digestion followed by filling in the overhangs using the Klenow fragment of DNA polymerase I to generate blunt ends. StyI cleaves at nucleotide 49 and BglII cleaves at nucleotide 1997 of SEQ ID NO: 5. The IL-1R cDNA fragment is ligated into the SmaI-digested SF CAV vector, and *E. coli* cells are transformed with the ligation mixture by standard procedures. The resulting vector is recovered from the *E. coli* cells and used as the template in the PCR reaction.

The 5' primer (SEQ ID NO:18) corresponds to a 17-nucleotide sequence found in the vector upstream of the inserted IL-1R cDNA. The 3' primer (SEQ ID NO:19) includes a segment complementary to nucleotides 1060–1079 of SEQ ID NO:5, which encode amino acids 306 (partial codon) through 312, near the C-terminus of the IL-1R extracellular domain. This 3' primer also contains a sequence encoding the peptide linker Gly$_4$SerGly$_5$Ser (SEQ ID NO:23).

A PCR reaction is conducted using any suitable procedure, such as those described in Sarki et al., *Science* 239:487 (1988); in *Recombinant DNA Methodology*, Wu et al., eds., Academic Press Inc., San Diego (1989), pp. 189–196; and in *PCR Protocols: A Guide to Methods and Applications*, Innis et al., eds., Academic Press, Inc. (1990). An example of a suitable PCR procedure is as follows. All temperatures are in degrees centigrade. The following PCR reagents are added to a 0.5 ml Eppendorf microfuge tube: 10 µl of 10×PCR buffer (500 mM KCl, 100 mM Tris-HCl, pH 8.3 at 25° C., 25 mM MgCl$_2$, and 1 mg/ml gelatin) (Perkin-Elmer Cetus, Norwalk, Conn.), 8 µl of a 2.5 mM solution containing each dNTP (2 mM DATP, 2 mM dCTP, 2 mM dGTP and 2 mM dTTP), 2.5 units (0.5 µl of standard 5000 units/ml solution) of Taq DNA polymerase (Perkins-Elmer Cetus), 1 ng of template DNA, 100 picomoles of each of the oligonucleotide primers, and water to a final volume of 100 µl. The final mixture is then overlaid with 100 µl parafin oil. PCR is carried out using a DNA thermal cycler (Ericomp, San Diego, Calif.). The template is denatured at 94°, for 5 minutes and PCR is carried out for 25 cycles of amplification using a step program (denaturation at 94°, 1.5 minutes; annealing at 60°, 1 minute; extension at 72°, 1 minute).

Electrophoresis of an aliquot of the reaction mixture on 1% SeaKem low melting temperature (LMT) agarose (FMC BioProducts, Rockland, Me.) and staining with ethidium bromide visualizes a single DNA fragment of the expected size as the PCR reaction product. The PCR-amplified DNA fragment comprises a short vector sequence that includes an Asp718 restriction site, upstream of a sequence encoding IL-1R amino acids 1(Asp) to 312 (Thr), followed by a single stranded segment encoding the peptide linker.

A second PCR reaction is conducted to isolate and amplify a cDNA fragment encoding a soluble TNF-R polypeptide. The template was the vector designated psolhuTNF-R Δ235/CAVNOT in example 4, which contains a cDNA insert encoding TNF-R amino acids −22 to 235 of SEQ ID NO: 1. The primers employed in the reaction are:

5' GGTGGCGGTGGATCCGGCGGTGGCGGCG-
    GCTCATTGCCCGCCCAGGTGGCA 3'  SEQ ID NO: 20

3' TGACGCGCGACTCGTTCG 5'  SEQ ID NO: 21

The 5' primer (SEQ ID NO: 20) comprises a peptide linker encoding segment complementary to the peptide linker encoding portion of the SEQ ID NO: 19 primer. The linker-encoding segment is followed by codons for the first six amino acids of mature TNF-R (Leu through Ala).

The 3' primer (SEQ ID NO: 21) comprises nucleotides complementary to nucleotides 461–478 of TNF-R SEQ ID NO: 1, which encode amino acids 103 (Tyr, partial codon) through 109 (Gln, partial codon). This primer also encompasses an EspI restriction site that is naturally present in this portion of the TNF-R protein.

The PCR reaction procedure is as described above. The DNA fragment amplified by this second PCR reaction comprises the above-described linker-encoding segment followed by a sequence encoding amino acids 1 (Leu) through 109 (Gln, partial codon) of TNF-R. This DNA fragment is visualized by electrophoresis followed by ethidium bromide staining of the gel, as described above. A third PCR reaction is conducted to isolate an amplified double stranded DNA fragment comprising IL-1R and TNF-R sequences separated by the linker sequence. The following reagents were combined in a 0.5 ml. tube:

3 µl (about 5–10 ng) of the IL-1R-peptide linker DNA fragment amplified in the first PCR reaction above—a 3 µl aliquot is taken directly from the LMT agarose by micropipette, using UV light to visualize the desired band on the ethidium bromide stained gel 3 µl (about 5–10 ng) of the peptide linker-TNF-R DNA fragment amplified in the second PCR reaction above—a 3 µl aliquot is micropipetted directly from the region of the LMT agarose gel that contains the desired band 10 µl of 10×PCR buffer (described above)

100 pmole of the SEQ ID NO: 18 oligonucleotide as the 5' primer 100 pmole of the SEQ ID NO: 21 oligonucleotide as the 3' primer 4 µl of a 2.5 mM solution containing each of the four dNTPs 0.5 µl of Taq DNA polymerase (5 units/µl)

water to a final volume of 100 µl

The PCR reaction cycles are conducted at the temperatures and for the time periods specified above. After the initial denaturing step, the complementary peptide linker-encoding segments of the two DNA fragments anneal. The end product of the reaction is a blunt-ended double-stranded amplified DNA fragment about 1370 bp in length, comprising an IL-1R DNA sequence upstream of a sequence encoding a peptide linker, followed by a TNF-R DNA sequence.

A 25 µl aliquot of this third PCR reaction mixture is, without purification, reacted with the restriction enzymes Asp718 and EspI. Asp 718 cleaves upstream of the IL-1R sequence, as discussed above. EspI cleaves within the TNF-R sequence, as shown in FIG. 2 and discussed above. The restriction endonuclease Cell II is an isoschizomer of EspI and may be substituted for EspI. The desired fragment, referred to as fragment E hereinafter, is purified by conventional procedures such as separation by gel electrophoresis, e.g., on a 1.0% Seaplaque low melting temperature agarose gel, and isolation of the band representing the desired fragment.

Figure 4:
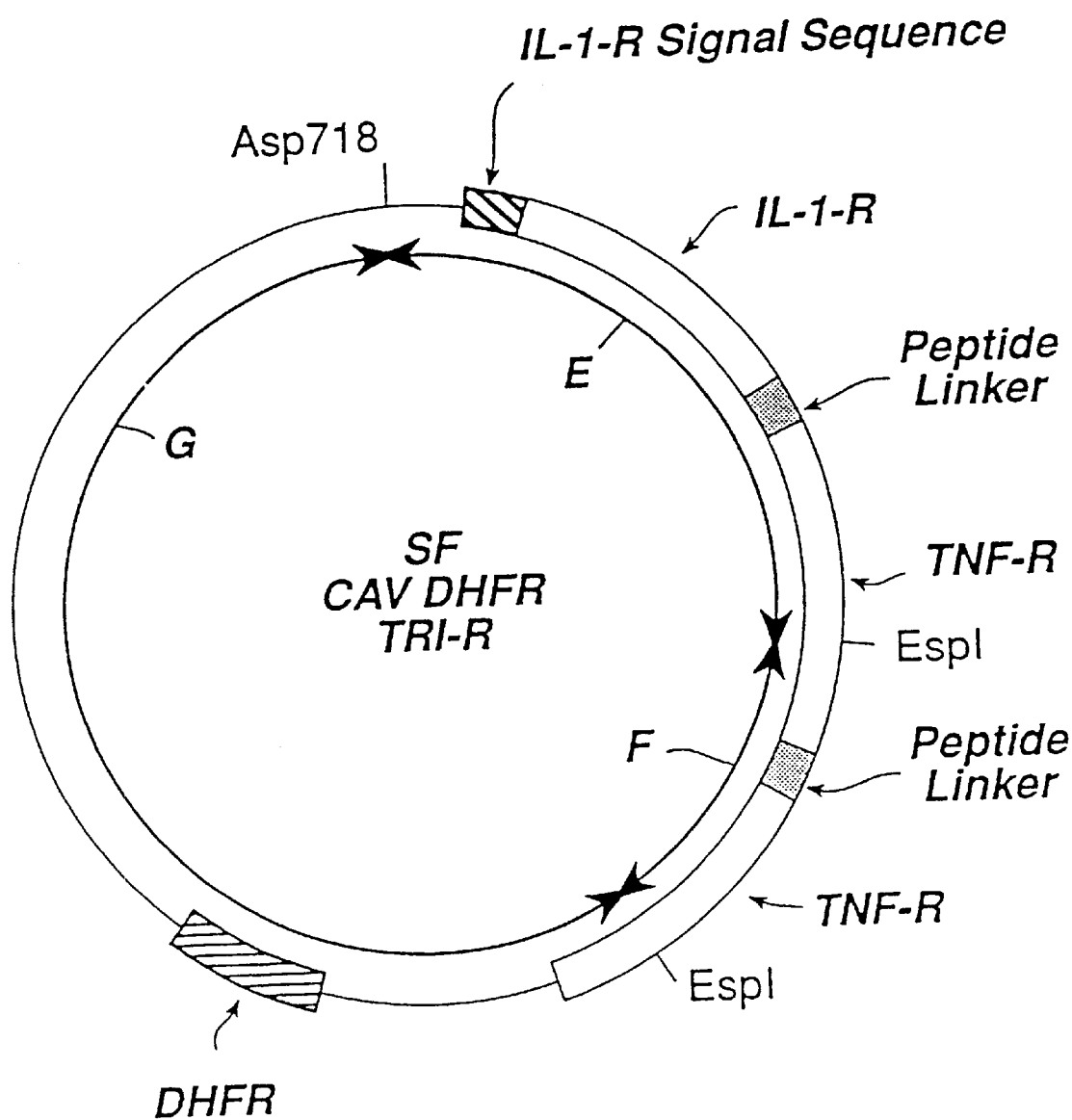
FIG. 4 depicts a plasmid vector comprising a DNA fragment encoding a fusion protein of the formula IL-1R-linker-TNF-R-linker-TNF-R, constructed as described in example 12.

Two additional DNA fragments designated F and G are isolated and joined with fragment E to construct an expression vector having a second TNF-R sequence fused (via a peptide linker sequence) downstream of the IL-1R-linker-TNF-R DNA fragment prepared above. The resulting vector and the positions of fragments E, F, and G contained therein are depicted in FIG. 4.

The DNA fragment designated F is prepared by digesting the vector depicted in FIG. 3 and constructed in example 11 with EspI. A fragment containing a 3' portion of TNF-R (extending from the EspI site shown in FIG. 2 through a codon for amino acid 235) followed by a sequence encoding a Gly$_4$SerGly$_5$Ser (SEQ ID NO:23) peptide linker that is followed by a second TNF-R sequence extending from the codon for amino acid 1 (Leu) to the EspI site in the second (downstream) TNF-R sequence of the FIG. 3 vector, is isolated. This fragment, about 739 base pairs in length, is designated fragment F hereinafter.

Fragment G, containing vector sequences (including DHFR) and a 3' portion of a TNF-R sequence is isolated from a "splice free" vector as follows. The pCAV/DHFR/TNF-R vector prepared in example 11 contains a sequence which is believed to be disadvantageous for construction of IL-1R-encoding vectors, possibly because of a cryptic promoter within this sequence from which undesired protein is expressed in E. coli. A derivative of pCAV/DHFR/TNF-R was prepared by replacing an NdeI/Asp 718 vector fragment that contains the undesirable sequence with an NdeI/Asp 718 fragment from splice free vector SF CAV (ATCC 68922, described above). The construction is depicted in FIG. 5.

Figure 5:
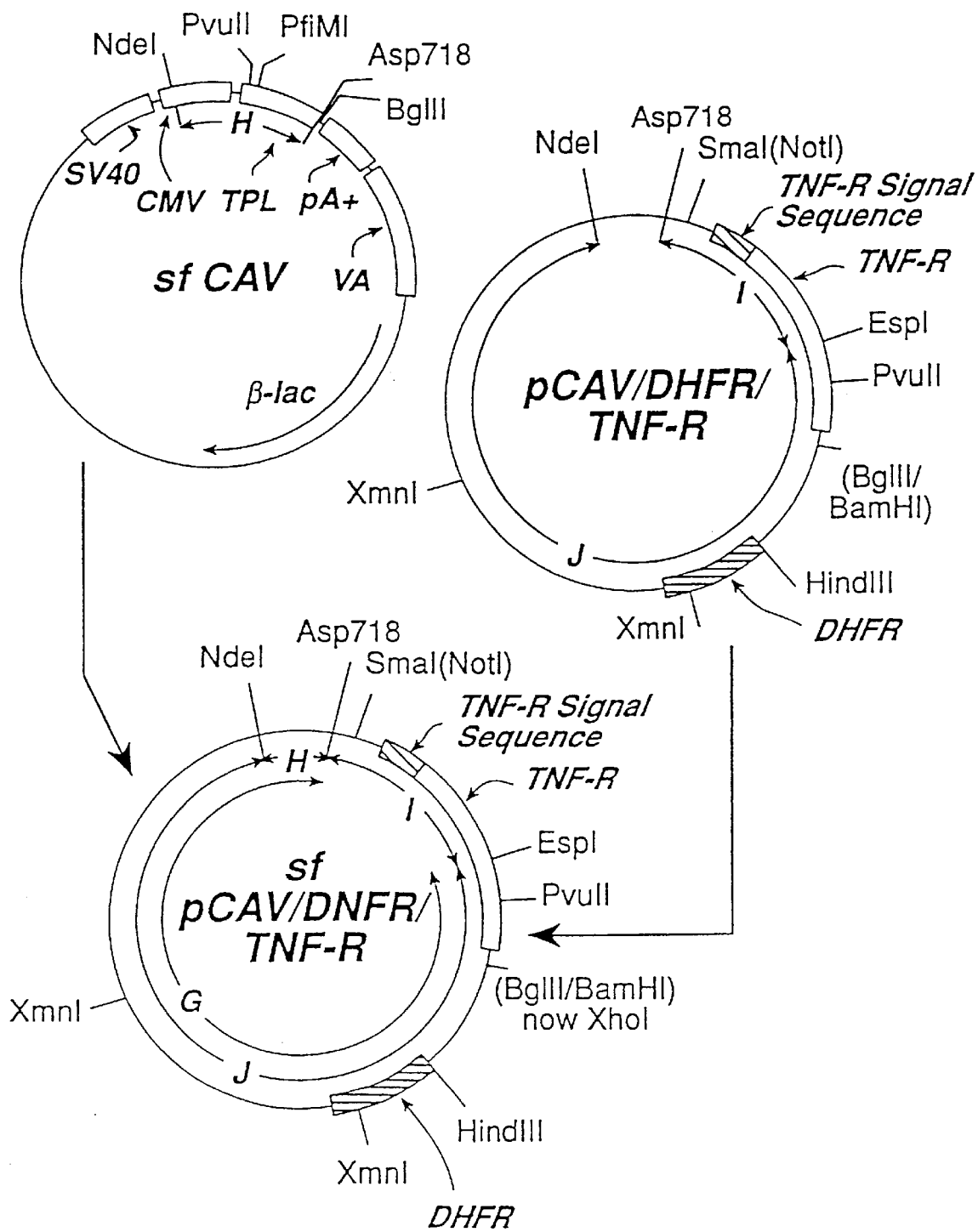
FIG. 5 depicts three plasmid vectors that are intermediates in the construction of certain vectors of the present invention, as described in example 12.

SF CAV is digested with NdeI and Asp 718 (unique sites in this plasmid) and the fragment of about 500 bp labeled H in FIG. 5 is isolated. Fragment H lacks the undesired sequence found in the corresponding fragment of pCAV/DHFR/TNF-R.

The pCAV/DHFR/TNF-R vector prepared in example 11 and shown in FIG. 5 is digested with Asp 718, EspI, and NdeI. An Asp 718/EspI fragment of about 495 bp is isolated (fragment I). An NdeI/EspI fragment of about 4647 bp is also isolated (fragment J).

DNA fragments H, I, and J prepared above are ligated together to form the splice free vector SF CAV/DHFR/TNF-R shown in FIG. 5. E. coli cells are transformed with the ligation mixture by conventional procedures. Plasmid DNA is recovered from the host cells and the desired construct is confirmed by restriction analysis. SF pCAV/DHFR/TNF-R is then digested with Asp718 and EspI. The fragment designated G in FIG. 5 contains vector sequences (including DHFR) and the 3' end of a TNF-R sequence (from the internal EspI site through the codon for amino acid 235 followed by a stop codon) and is isolated by conventional procedures.

DNA fragments E, F, and G prepared above are ligated together to form the vector depicted in FIG. 4 (and designated SF CAV DHFR tri-R). E coli cells are transformed with the ligation mixture and the desired plasmid is recovered as described above. The fusion protein encoded by this vector comprises (from N- to C-terminus) amino acids -20 to 312 of type I IL-1R; a Gly$_4$SerGly$_4$Ser (SEQ ID NO:29) peptide linker; amino acids 1 to 235 of TNF-R; a Gly$_4$SerGly$_5$Ser (SEQ ID NO:23) peptide linker; and a second TNF-R polypeptide comprising amino acids 1 to 235.

Mammalian cells are transfected with the expression vector by conventional procedures and cultured to produce the desired fusion protein. One suitable mammalian cell line is a DHFR$^-$ Chinese hamster ovary cell line designated CHO-K1 and available from the American Type Culture Collection, Rockville, Md., under accession number CCL61. The cells may be transfected with the expression vector by standard calcium phosphate precipitation, essentially as described by Graham and van der Eb, Virology 52:456 (1983). The transfected cells are cultured under suitable conventional conditions, and the presence of the desired fusion protein in the culture medium is confirmed by assays such as those described in examples 1 and 2.

Example 13

Fusion Protein Comprising One IL-1R Polypeptide and One TNF-R Polypeptide

Fragments E and G prepared in example 12 may be ligated together to form a vector containing a DNA sequence that encodes a fusion protein of the formula IL-1R-peptide linker-TNF-R, wherein the peptide linker is Gly$_4$SerGly$_5$Ser (SEQ ID NO:23). IL-1R and TNF-R are soluble polypeptides as described in example 12. The fusion protein of example 12 is preferred due to the enhanced TNF binding achieved when two, rather than one, TNF-R polypeptides are employed.

The skilled artisan will appreciate that the techniques disclosed herein may be employed to produce additional fusion proteins of the present invention, beyond those illustrative embodiments presented in the foregoing examples. The peptide linker may be varied by synthesizing an oligonucleotide encoding a different peptide linker sequence, for example. Further, alternative fragments of the IL-1R or TNF-R proteins may be isolated by employing PCR primers that anneal to a different desired portion of the disclosed DNA sequences thus defining the termini of the desired fragment. Oligonucleotides used to regenerate a terminus of a DNA fragment (e.g., the oligonucleotide employed in example 4) may be varied to position a stop codon after any desired amino acid. Further, the choice of expression vector will depend upon the intended host cells.

BRIEF DESCRIPTION OF THE SEQUENCE LISTING

SEQ ID NO: 1 and SEQ ID NO: 2 show the nucleotide sequence and encoded amino acid sequence of a human TNF-R cDNA. The mature protein is defined by amino acids 1–439. The signal peptide is defined by amino acids -22 through -1. The transmembrane region is defined by amino acids 236–265.

SEQ ID NO: 3 and SEQ ID NO: 4 show the nucleotide sequence and encoded amino acid sequence of the coding region of a human TNF-R cDNA. This TNF-R is a different protein from the TNF-R of SEQ ID NOS: 1 and 2. The mature protein is defined by amino acids 1–415. The signal peptide is defined by amino acids -40 through -1. The transmembrane region is defined by amino acids 172–192.

SEQ ID NO: 5 and SEQ ID NO: 6 show the nucleotide sequence and encoded amino acid sequence of a human type I IL-1R cDNA. The mature protein is defined by amino acids 1–549. The predicted signal peptide is defined by amino acids -20 through -1. The transmembrane region is defined by amino acids 317–336.

SEQ ID NO: 7 and SEQ ID NO: 8 show the nucleotide sequence and encoded amino acid sequence of a human type II IL-1R cDNA. The mature protein is defined by amino acids 1–385. The predicted signal peptide is defined by amino acids -13 through -1. The transmembrane region is defined by amino acids 331–356.

SEQ ID NOS: 9–15 and 18–21 depict oligonucleotides employed in constructing various recombinant plasmids, as described in the examples section.

SEQ ID NOS: 16 and 17 depict an oligonucleotide and the amino acid sequence encoded thereby, which includes a Gly$_4$SerGly$_5$Ser (SEQ ID NO:23) peptide linker sequence. This oligonucleotide is employed in the vector construction described in example 11.

What is claimed is:

1. An isolated DNA molecule that encodes a fusion protein comprising two tumor necrosis factor receptor (TNFR) polypeptides and one interleukin-1 receptor (IL-1R) polypeptide, wherein said fusion protein is of a formula selected from:

TNFR-linker-TNFR-linker-IL-1R;

and

IL-1R-linker-TNFR-linker-TNFR, wherein each linker is a peptide linker; and wherein each TNFR represents a soluble TNFR.

2. An expression vector comprising DNA having the sequence of a molecule according to claim 1.

3. A host cell containing an expression vector according to claim 2.

4. A DNA molecule that encodes a fusion protein comprising a human tumor necrosis factor receptor (TNFR) polypeptide, said protein of the formula:

TNF-linker-TNFR, wherein the linker is a peptide linker; and wherein each TNFR represents a soluble TNFR.

5. An expression vector comprising DNA having the sequence of a molecule according to claim 4.

6. A host cell containing an expression vector according to claim 5.

7. A process for producing a fusion protein of the formula:

TNF-R-linker-TNF-R-linker-IL-1R or

IL-1R-linker-TNF-R-linker-TNF-R comprising culturing a host cell according to claim 3 under conditions that promote expression of said fusion protein, and recovering said fusion protein.

8. A process for producing a fusion protein of the formula THF-R-peptide linker-TNF-R comprising culturing a host cell according to claim 6 under conditions that promotes expression of said fusion protein, and recovering said fusion protein.

9. A fusion protein comprising two human tumor necrosis factor receptor (TNFR) polypeptides and a human interleukin-1 receptor (IL-1R) wherein said fusion protein is of a formula selected from:

TNFR-linker-TNFR-linker-IL-1R and

IL-1R-linker-TNFR-linker-TNFR wherein each linker is a peptide linker; and wherein each TNFR represents a soluble TNFR.

10. A fusion protein according to claim 9, wherein each of the peptide linkers comprises from 5 to 100 amino acid residues independently selected from the group consisting of glycine, asparagine, serine, threonine, and alanine.

11. A fusion protein according to claim 9, wherein IL-1R represents a soluble IL-1R.

12. A fusion protein according to claim 9, wherein each soluble TNFR comprises the amino acid sequence 1–163 of SEQ ID NO:2.

13. A fusion protein according to claim 11, wherein the soluble IL-1R comprises amino acid sequence 1–312 of SEQ ID NO:6.

14. A fusion protein according to claim 11, wherein the soluble IL-1R comprises the amino acid sequence 1–330 of SEQ ID NO:8.

15. A fusion protein of the formula:

TNFR-linker-TNFR wherein the linker is a peptide linker; and wherein each TNFR represents a soluble TNFR.

16. A fusion protein according to claim 15, wherein the peptide linker comprises from 5 to 100 amino acid residues independently selected from the group consisting of glycine, asparagine, serine, threonine, and alanine.

17. A fusion protein according to claim 15, wherein each soluble TNFR comprises the amino acid sequence 1–163 of SEQ ID NO:2.

18. A pharmaceutical composition comprising a fusion protein according to claim 9 and a suitable diluent, excipient, or carrier.

19. A pharmaceutical composition comprising a fusion protein according to claim 15 and a suitable diluent, excipient, or carrier.

20. A multimer having the ability to interfere with the binding of tumor necrosis factor to its receptors and to block the effects of tumor necrosis factor, wherein said multimer comprises two or more monomers, each said monomer consisting of a soluble form of a tumor necrosis factor receptor.

21. The multimer of claim 20, wherein said soluble form of a tumor necrosis factor receptor comprises amino acid 1–235 of SEQ ID NO:2.

22. An isolated DNA molecule that encodes a multimer having the ability to interfere with the binding of tumor necrosis factor to its receptors and to block the effects of tumor necrosis factor (TNF), wherein said multimer comprises two monomers, each said monomer consisting of a soluble form of a tumor necrosis factor receptor (TNFR).

23. The isolated DNA molecule of claim 22, wherein said soluble form of a TNFR comprises amino acid 1–235 of SEQ ID NO:2.

24. A bivalent TNFR molecule consisting of two tandem repeats of amino acids 1–235 of SEQ ID NO:2, separated by a linker region.

25. A polyvalent TNFR molecule of the formula:

$$(TNFR)_n\text{-polymer},$$

wherein the polymer is selected from the group consisting of Ficoll, polyethylene glycol and dextran, and wherein $TNFR_n$ represents more than one soluble tumor necrosis factor receptor polypeptide.

26. A tetravalent TNFR molecule of the formula:

$$(TNFR\text{-biotin})_4\text{-avidin},$$

wherein TNFR represents a soluble tumor necrosis factor receptor polypeptide.

27. A decavalent TNFR molecule of the formula:

$$(TNFR\text{-DNP})_{10}\text{-anti-DNP-IgM},$$

wherein DNP represent dinitrophenol, and TNFR represents a soluble tumor necrosis factor receptor polypeptide, or of the formula:

$$(TNFR\text{-TNP})_{10}\text{-anti-TNP-IgM},$$

wherein TNP represent trinitrophenol, and TNFR represents a soluble tumor necrosis factor receptor polypeptide.

28. A polyvalent TNFR molecule obtained by the process comprising chemically coupling TNFRs to a polymer to obtain said polyvalent TNFR molecule, wherein the polymer is selected from the group consisting of Ficoll, polyethylene glycol and dextran, and wherein TNFR represents a soluble tumor necrosis factor receptor polypeptide.

29. A tetravalent TNFR molecule obtained by the process comprising:

(A) chemically coupling TNFR to biotin to obtain a biotin-TNFR conjugate, wherein TNFR represents a soluble tumor necrosis factor receptor polypeptide; and (B) allowing four molecules of the resulting conjugate to bind to avidin to form said tetravalent TNFR molecule.

30. A decavalent TNFR molecule obtained by the process comprising:

(A) chemically coupling TNFR to dinitrophenol (DNP) or trinitrophenol (TNP) to form a TNFR-DNP or TNFR-TNP conjugate, wherein TNFR represents a soluble tumor necrosis factor receptor polypeptide; and (B) precipitating the resulting conjugate with anti-DNP-IgM or anti-TNP-IgM, respectively, to form decameric conjugates with a valency of 10 for TNFR binding sites.

* * * * *

UNITED STATES PATENT AND TRADEMARK OFFICE
CERTIFICATE OF CORRECTION

PATENT NO.     : 6,541,610 B1
DATED          : April 1, 2003
INVENTOR(S)    : Craig A. Smith, Raymond G. Goodwin and Patricia M. Beckmann It is certified that error appears in the above-identified patent and that said Letters Patent is hereby corrected as shown below:

<u>Title page,</u>
Item [63], Related U.S. Application Data,
"[63]  Continuation of application No. 08/255,849, filed Jun. 8, 1994, now abandoned, which is a continuation-in-part of application No. 07/523,635, filed May 10, 1990, now Pat. No. 5,395,760, which is a continuation-in-part of application No. 07/421,417, filed Oct. 13, 1989, now abandoned, which is a continuation-in-part of application No. 07/405,370, filed Sep. 11, 1989, now abandoned, which is a continuation-in-part of application No. 07/403,241, filed on Sep. 5, 1989, now abandoned." should be
-- [63]  Continuation of application No. 08/255,849, filed Jun. 8, 1994, now abandoned, which is a continuation of application No. 07/860,710, filed Mar. 30, 1992, now abandoned, which is a continuation-in-part of application No. 07/523,635, filed May 10, 1990, now Pat. No. 5,395,760, which is a continuation-in-part of application No. 07/421,417, filed Oct. 13, 1989, now abandoned, which is a continuation-in-part of application No. 07/405,370, filed Sep. 11, 1989, now abandoned, which is a continuation-in-part of application No. 07/403,241, filed on Sep. 5, 1989, now abandoned. --

Signed and Sealed this

Twenty-third Day of September, 2003

JAMES E. ROGAN
*Director of the United States Patent and Trademark Office*

SEQUENCE LISTING

<160> NUMBER OF SEQ ID NOS: 29

<210> SEQ ID NO 1
<211> LENGTH: 1641
<212> TYPE: DNA
<213> ORGANISM: Homo sapiens
<220> FEATURE:
<221> NAME/KEY: mat_peptide
<222> LOCATION: (154)..()
<223> OTHER INFORMATION:
<220> FEATURE:
<221> NAME/KEY: CDS
<222> LOCATION: (88)..(1470)
<223> OTHER INFORMATION:
<220> FEATURE:
<221> NAME/KEY: sig_peptide
<222> LOCATION: (88)..(153)
<223> OTHER INFORMATION:

<400> SEQUENCE: 1

```
gcgaggcagg cagcctggag agaaggcgct gggctgcgag ggcgcgaggg cgcgagggca        60
gggggcaacc ggaccccgcc cgcatcc atg gcg ccc gtc gcc gtc tgg gcc gcg       114
                                Met Ala Pro Val Ala Val Trp Ala Ala
                                    -20                 -15 ctg gcc gtc gga ctg gag ctc tgg gct gcg gcg cac gcc ttg ccc gcc         162
Leu Ala Val Gly Leu Glu Leu Trp Ala Ala Ala His Ala Leu Pro Ala
        -10                 -5              -1  1 cag gtg gca ttt aca ccc tac gcc ccg gag ccc ggg agc aca tgc cgg         210
Gln Val Ala Phe Thr Pro Tyr Ala Pro Glu Pro Gly Ser Thr Cys Arg
    5                  10                  15 ctc aga gaa tac tat gac cag aca gct cag atg tgc tgc agc aaa tgc         258
Leu Arg Glu Tyr Tyr Asp Gln Thr Ala Gln Met Cys Cys Ser Lys Cys
20                  25                  30                  35 tcg ccg ggc caa cat gca aaa gtc ttc tgt acc aag acc tcg gac acc         306
Ser Pro Gly Gln His Ala Lys Val Phe Cys Thr Lys Thr Ser Asp Thr
                40                  45                  50 gtg tgt gac tcc tgt gag gac agc aca tac acc cag ctc tgg aac tgg         354
Val Cys Asp Ser Cys Glu Asp Ser Thr Tyr Thr Gln Leu Trp Asn Trp
            55                  60                  65 gtt ccc gag tgc ttg agc tgt ggc tcc cgc tgt agc tct gac cag gtg         402
Val Pro Glu Cys Leu Ser Cys Gly Ser Arg Cys Ser Ser Asp Gln Val
        70                  75                  80 gaa act caa gcc tgc act cgg gaa cag aac cgc atc tgc acc tgc agg         450
Glu Thr Gln Ala Cys Thr Arg Glu Gln Asn Arg Ile Cys Thr Cys Arg
    85                  90                  95 ccc ggc tgg tac tgc gcg ctg agc aag cag gag ggg tgc cgg ctg tgc         498
Pro Gly Trp Tyr Cys Ala Leu Ser Lys Gln Glu Gly Cys Arg Leu Cys
100                 105                 110                 115 gcg ccg ctg cgc aag tgc cgc ccg ggc ttc ggc gtg gcc aga cca gga         546
Ala Pro Leu Arg Lys Cys Arg Pro Gly Phe Gly Val Ala Arg Pro Gly
                120                 125                 130 act gaa aca tca gac gtg gtg tgc aag ccc tgt gcc ccg ggg acg ttc         594
Thr Glu Thr Ser Asp Val Val Cys Lys Pro Cys Ala Pro Gly Thr Phe
            135                 140                 145 tcc aac acg act tca tcc acg gat att tgc agg ccc cac cag atc tgt         642
Ser Asn Thr Thr Ser Ser Thr Asp Ile Cys Arg Pro His Gln Ile Cys
        150                 155                 160 aac gtg gtg gcc atc cct ggg aat gca agc atg gat gca gtc tgc acg         690
Asn Val Val Ala Ile Pro Gly Asn Ala Ser Met Asp Ala Val Cys Thr
    165                 170                 175 tcc acg tcc ccc acc cgg agt atg gcc cca ggg gca gta cac tta ccc         738
```

-continued

```
Ser Thr Ser Pro Thr Arg Ser Met Ala Pro Gly Ala Val His Leu Pro
180                 185                 190                 195 cag cca gtg tcc aca cga tcc caa cac acg cag cca act cca gaa ccc       786
Gln Pro Val Ser Thr Arg Ser Gln His Thr Gln Pro Thr Pro Glu Pro
                200                 205                 210 agc act gct cca agc acc tcc ttc ctg ctc cca atg ggc ccc agc ccc       834
Ser Thr Ala Pro Ser Thr Ser Phe Leu Leu Pro Met Gly Pro Ser Pro
            215                 220                 225 cca gct gaa ggg agc act ggc gac ttc gct ctt cca gtt gga ctg att       882
Pro Ala Glu Gly Ser Thr Gly Asp Phe Ala Leu Pro Val Gly Leu Ile
        230                 235                 240 gtg ggt gtg aca gcc ttg ggt cta cta ata ata gga gtg gtg aac tgt       930
Val Gly Val Thr Ala Leu Gly Leu Leu Ile Ile Gly Val Val Asn Cys
    245                 250                 255 gtc atc atg acc cag gtg aaa aag aag ccc ttg tgc ctg cag aga gaa       978
Val Ile Met Thr Gln Val Lys Lys Lys Pro Leu Cys Leu Gln Arg Glu
260                 265                 270                 275 gcc aag gtg cct cac ttg cct gcc gat aag gcc cgg ggt aca cag ggc      1026
Ala Lys Val Pro His Leu Pro Ala Asp Lys Ala Arg Gly Thr Gln Gly
                280                 285                 290 ccc gag cag cag cac ctg ctg atc aca gcg ccg agc tcc agc agc agc      1074
Pro Glu Gln Gln His Leu Leu Ile Thr Ala Pro Ser Ser Ser Ser Ser
            295                 300                 305 tcc ctg gag agc tcg gcc agt gcg ttg gac aga agg gcg ccc act cgg      1122
Ser Leu Glu Ser Ser Ala Ser Ala Leu Asp Arg Arg Ala Pro Thr Arg
        310                 315                 320 aac cag cca cag gca cca ggc gtg gag gcc agt ggg gcc ggg gag gcc      1170
Asn Gln Pro Gln Ala Pro Gly Val Glu Ala Ser Gly Ala Gly Glu Ala
    325                 330                 335 cgg gcc agc acc ggg agc tca gat tct tcc cct ggt ggc cat ggg acc      1218
Arg Ala Ser Thr Gly Ser Ser Asp Ser Ser Pro Gly Gly His Gly Thr
340                 345                 350                 355 cag gtc aat gtc acc tgc atc gtg aac gtc tgt agc agc tct gac cac      1266
Gln Val Asn Val Thr Cys Ile Val Asn Val Cys Ser Ser Ser Asp His
                360                 365                 370 agc tca cag tgc tcc tcc caa gcc agc tcc aca atg gga gac aca gat      1314
Ser Ser Gln Cys Ser Ser Gln Ala Ser Ser Thr Met Gly Asp Thr Asp
            375                 380                 385 tcc agc ccc tcg gag tcc ccg aag gac gag cag gtc ccc ttc tcc aag      1362
Ser Ser Pro Ser Glu Ser Pro Lys Asp Glu Gln Val Pro Phe Ser Lys
        390                 395                 400 gag gaa tgt gcc ttt cgg tca cag ctg gag acg cca gag acc ctg ctg      1410
Glu Glu Cys Ala Phe Arg Ser Gln Leu Glu Thr Pro Glu Thr Leu Leu
    405                 410                 415 ggg agc acc gaa gag aag ccc ctg ccc ctt gga gtg cct gat gct ggg      1458
Gly Ser Thr Glu Glu Lys Pro Leu Pro Leu Gly Val Pro Asp Ala Gly
420                 425                 430                 435 atg aag ccc agt taaccaggcc ggtgtgggct gtgtcgtagc caaggtgggc          1510
Met Lys Pro Ser tgagccctgg caggatgacc ctgcgaaggg gccctggtcc ttccaggccc ccaccactag    1570
gactctgagg ctctttctgg gccaagttcc tctagtgccc tccacagccg cagcctccct   1630
ctgacctgca g                                                         1641

<210> SEQ ID NO 2
<211> LENGTH: 461
<212> TYPE: PRT
<213> ORGANISM: Homo sapiens

<400> SEQUENCE: 2
```

```
Met Ala Pro Val Ala Val Trp Ala Leu Ala Val Gly Leu Glu Leu
        -20              -15              -10

Trp Ala Ala Ala His Ala Leu Pro Ala Gln Val Ala Phe Thr Pro Tyr
 -5              -1   1               5                      10

Ala Pro Glu Pro Gly Ser Thr Cys Arg Leu Arg Glu Tyr Tyr Asp Gln
            15              20              25

Thr Ala Gln Met Cys Cys Ser Lys Cys Ser Pro Gly Gln His Ala Lys
             30              35              40

Val Phe Cys Thr Lys Thr Ser Asp Thr Val Cys Asp Ser Cys Glu Asp
         45              50              55

Ser Thr Tyr Thr Gln Leu Trp Asn Trp Val Pro Glu Cys Leu Ser Cys
         60              65              70

Gly Ser Arg Cys Ser Ser Asp Gln Val Glu Thr Gln Ala Cys Thr Arg
 75              80              85                      90

Glu Gln Asn Arg Ile Cys Thr Cys Arg Pro Gly Trp Tyr Cys Ala Leu
             95              100             105

Ser Lys Gln Glu Gly Cys Arg Leu Cys Ala Pro Leu Arg Lys Cys Arg
            110             115             120

Pro Gly Phe Gly Val Ala Arg Pro Gly Thr Glu Thr Ser Asp Val Val
         125             130             135

Cys Lys Pro Cys Ala Pro Gly Thr Phe Ser Asn Thr Thr Ser Ser Thr
140             145             150

Asp Ile Cys Arg Pro His Gln Ile Cys Asn Val Val Ala Ile Pro Gly
155             160             165             170

Asn Ala Ser Met Asp Ala Val Cys Thr Ser Thr Ser Pro Thr Arg Ser
            175             180             185

Met Ala Pro Gly Ala Val His Leu Pro Gln Pro Val Ser Thr Arg Ser
            190             195             200

Gln His Thr Gln Pro Thr Pro Glu Pro Ser Thr Ala Pro Ser Thr Ser
        205             210             215

Phe Leu Leu Pro Met Gly Pro Ser Pro Pro Ala Glu Gly Ser Thr Gly
        220             225             230

Asp Phe Ala Leu Pro Val Gly Leu Ile Val Gly Val Thr Ala Leu Gly
235             240             245             250

Leu Leu Ile Ile Gly Val Val Asn Cys Val Ile Met Thr Gln Val Lys
            255             260             265

Lys Lys Pro Leu Cys Leu Gln Arg Glu Ala Lys Val Pro His Leu Pro
            270             275             280

Ala Asp Lys Ala Arg Gly Thr Gln Gly Pro Glu Gln Gln His Leu Leu
            285             290             295

Ile Thr Ala Pro Ser Ser Ser Ser Ser Ser Leu Glu Ser Ser Ala Ser
            300             305             310

Ala Leu Asp Arg Arg Ala Pro Thr Arg Asn Gln Pro Gln Ala Pro Gly
315             320             325             330

Val Glu Ala Ser Gly Ala Gly Glu Ala Arg Ala Ser Thr Gly Ser Ser
            335             340             345

Asp Ser Ser Pro Gly Gly His Gly Thr Gln Val Asn Val Thr Cys Ile
            350             355             360

Val Asn Val Cys Ser Ser Ser Asp His Ser Ser Gln Cys Ser Ser Gln
            365             370             375

Ala Ser Ser Thr Met Gly Asp Thr Asp Ser Ser Pro Ser Glu Ser Pro
            380             385             390
```

```
Lys Asp Glu Gln Val Pro Phe Ser Lys Glu Glu Cys Ala Phe Arg Ser
395                 400                 405                 410

Gln Leu Glu Thr Pro Glu Thr Leu Leu Gly Ser Thr Glu Glu Lys Pro
                415                 420                 425

Leu Pro Leu Gly Val Pro Asp Ala Gly Met Lys Pro Ser
            430                 435

<210> SEQ ID NO 3
<211> LENGTH: 1368
<212> TYPE: DNA
<213> ORGANISM: Homo sapiens
<220> FEATURE:
<221> NAME/KEY: CDS
<222> LOCATION: (1)..(1365)
<223> OTHER INFORMATION:
<220> FEATURE:
<221> NAME/KEY: mat_peptide
<222> LOCATION: (121)..()
<223> OTHER INFORMATION:
<220> FEATURE:
<221> NAME/KEY: sig_peptide
<222> LOCATION: (1)..(120)
<223> OTHER INFORMATION:

<400> SEQUENCE: 3 atg ggc ctc tcc acc gtg cct gac ctg ctg ctg ccg ctg gtg ctc ctg      48
Met Gly Leu Ser Thr Val Pro Asp Leu Leu Leu Pro Leu Val Leu Leu
-40                 -35                 -30                 -25 gag ctg ttg gtg gga ata tac ccc tca ggg gtt att gga ctg gtc cct      96
Glu Leu Leu Val Gly Ile Tyr Pro Ser Gly Val Ile Gly Leu Val Pro
                -20                 -15                 -10 cac cta ggg gac agg gag aag aga gat agt gtg tgt ccc caa gga aaa     144
His Leu Gly Asp Arg Glu Lys Arg Asp Ser Val Cys Pro Gln Gly Lys
            -5                  -1  1                   5 tat atc cac cct caa aat aat tcg att tgc tgt acc aag tgc cac aaa     192
Tyr Ile His Pro Gln Asn Asn Ser Ile Cys Cys Thr Lys Cys His Lys
        10                  15                  20 gga acc tac ttg tac aat gac tgt cca ggc ccg ggg cag gat acg gac     240
Gly Thr Tyr Leu Tyr Asn Asp Cys Pro Gly Pro Gly Gln Asp Thr Asp
25                  30                  35                  40 tgc agg gag tgt gag agc ggc tcc ttc acc gct tca gaa aac cac ctc     288
Cys Arg Glu Cys Glu Ser Gly Ser Phe Thr Ala Ser Glu Asn His Leu
                45                  50                  55 aga cac tgc ctc agc tgc tcc aaa tgc cga aag gaa atg ggt cag gtg     336
Arg His Cys Leu Ser Cys Ser Lys Cys Arg Lys Glu Met Gly Gln Val
                60                  65                  70 gag atc tct tct tgc aca gtg gac cgg gac acc gtg tgt ggc tgc agg     384
Glu Ile Ser Ser Cys Thr Val Asp Arg Asp Thr Val Cys Gly Cys Arg
        75                  80                  85 aag aac cag tac cgg cat tat tgg agt gaa aac ctt ttc cag tgc ttc     432
Lys Asn Gln Tyr Arg His Tyr Trp Ser Glu Asn Leu Phe Gln Cys Phe
90                  95                  100 aat tgc agc ctc tgc ctc aat ggg acc gtg cac ctc tcc tgc cag gag     480
Asn Cys Ser Leu Cys Leu Asn Gly Thr Val His Leu Ser Cys Gln Glu
105                 110                 115                 120 aaa cag aac acc gtg tgc acc tgc cat gca ggt ttc ttt cta aga gaa     528
Lys Gln Asn Thr Val Cys Thr Cys His Ala Gly Phe Phe Leu Arg Glu
                125                 130                 135 aac gag tgt gtc tcc tgt agt aac tgt aag aaa agc ctg gag tgc acg     576
Asn Glu Cys Val Ser Cys Ser Asn Cys Lys Lys Ser Leu Glu Cys Thr
                140                 145                 150 aag ttg tgc cta ccc cag att gag aat gtt aag gga act gag gac tca     624
Lys Leu Cys Leu Pro Gln Ile Glu Asn Val Lys Gly Thr Glu Asp Ser
```

|  |  |  |  |  |  |  |  |  |  |  |  |  |  |
|---|---|---|---|---|---|---|---|---|---|---|---|---|---|
|  |  | 155 |  |  |  | 160 |  |  |  | 165 |  |  |  |

```
ggc acc aca gtg ctg ttg ccc ctg gtc att ttc ttt ggt ctt tgc ctt        672
Gly Thr Thr Val Leu Leu Pro Leu Val Ile Phe Phe Gly Leu Cys Leu
    170                 175                 180 tta tcc ctc ctc ttc att ggt tta agt tat cgc tac caa cgg tgg aag        720
Leu Ser Leu Leu Phe Ile Gly Leu Ser Tyr Arg Tyr Gln Arg Trp Lys
185                 190                 195                 200 tcc aag ctc tac tcc att gtt tgt ggg aaa tcg aca cct gaa aaa gag        768
Ser Lys Leu Tyr Ser Ile Val Cys Gly Lys Ser Thr Pro Glu Lys Glu
                205                 210                 215 ggg gag ctt gaa gga act act act aag ccc ctg gcc cca aac cca agc        816
Gly Glu Leu Glu Gly Thr Thr Thr Lys Pro Leu Ala Pro Asn Pro Ser
    220                 225                 230 ttc agt ccc act cca ggc ttc acc ccc acc ctg ggc ttc agt ccc gtg        864
Phe Ser Pro Thr Pro Gly Phe Thr Pro Thr Leu Gly Phe Ser Pro Val
235                 240                 245 ccc agt tcc acc ttc acc tcc agc tcc acc tat acc ccc ggt gac tgt        912
Pro Ser Ser Thr Phe Thr Ser Ser Ser Thr Tyr Thr Pro Gly Asp Cys
    250                 255                 260 ccc aac ttt gcg gct ccc cgc aga gag gtg gca cca ccc tat cag ggg        960
Pro Asn Phe Ala Ala Pro Arg Arg Glu Val Ala Pro Pro Tyr Gln Gly
265                 270                 275                 280 gct gac ccc atc ctt gcg aca gcc ctc gcc tcc gac ccc atc ccc aac       1008
Ala Asp Pro Ile Leu Ala Thr Ala Leu Ala Ser Asp Pro Ile Pro Asn
                285                 290                 295 ccc ctt cag aag tgg gag gac agc gcc cac aag cca cag agc cta gac       1056
Pro Leu Gln Lys Trp Glu Asp Ser Ala His Lys Pro Gln Ser Leu Asp
    300                 305                 310 act gat gac ccc gcg acg ctg tac gcc gtg gtg gag aac gtg ccc ccg       1104
Thr Asp Asp Pro Ala Thr Leu Tyr Ala Val Val Glu Asn Val Pro Pro
315                 320                 325 ttg cgc tgg aag gaa ttc gtg cgg cgc cta ggg ctg agc gac cac gag       1152
Leu Arg Trp Lys Glu Phe Val Arg Arg Leu Gly Leu Ser Asp His Glu
    330                 335                 340 atc gat cgg ctg gag ctg cag aac ggg cgc tgc ctg cgc gag gcg caa       1200
Ile Asp Arg Leu Glu Leu Gln Asn Gly Arg Cys Leu Arg Glu Ala Gln
345                 350                 355                 360 tac agc atg ctg gcg acc tgg agg cgg cgc acg ccg cgg cgc gag gcc       1248
Tyr Ser Met Leu Ala Thr Trp Arg Arg Arg Thr Pro Arg Arg Glu Ala
                365                 370                 375 acg ctg gag ctg ctg gga cgc gtg ctc cgc gac atg gac ctg ctg ggc       1296
Thr Leu Glu Leu Leu Gly Arg Val Leu Arg Asp Met Asp Leu Leu Gly
    380                 385                 390 tgc ctg gag gac atc gag gag gcg ctt tgc ggc ccc gcc gcc ctc ccg       1344
Cys Leu Glu Asp Ile Glu Glu Ala Leu Cys Gly Pro Ala Ala Leu Pro
395                 400                 405 ccc gcg ccc agt ctt ctc aga tga                                       1368
Pro Ala Pro Ser Leu Leu Arg
    410                 415

<210> SEQ ID NO 4
<211> LENGTH: 455
<212> TYPE: PRT
<213> ORGANISM: Homo sapiens

<400> SEQUENCE: 4

Met Gly Leu Ser Thr Val Pro Asp Leu Leu Pro Leu Val Leu Leu
-40                 -35                 -30                 -25

Glu Leu Leu Val Gly Ile Tyr Pro Ser Gly Val Ile Gly Leu Val Pro
                -20                 -15                 -10
```

```
His Leu Gly Asp Arg Glu Lys Arg Asp Ser Val Cys Pro Gln Gly Lys
        -5              -1   1              5

Tyr Ile His Pro Gln Asn Asn Ser Ile Cys Cys Thr Lys Cys His Lys
     10              15              20

Gly Thr Tyr Leu Tyr Asn Asp Cys Pro Gly Pro Gly Gln Asp Thr Asp
 25              30              35              40

Cys Arg Glu Cys Glu Ser Gly Ser Phe Thr Ala Ser Glu Asn His Leu
             45              50              55

Arg His Cys Leu Ser Cys Ser Lys Cys Arg Lys Glu Met Gly Gln Val
             60              65              70

Glu Ile Ser Ser Cys Thr Val Asp Arg Asp Thr Val Cys Gly Cys Arg
         75              80              85

Lys Asn Gln Tyr Arg His Tyr Trp Ser Glu Asn Leu Phe Gln Cys Phe
 90              95             100

Asn Cys Ser Leu Cys Leu Asn Gly Thr Val His Leu Ser Cys Gln Glu
105             110             115             120

Lys Gln Asn Thr Val Cys Thr Cys His Ala Gly Phe Phe Leu Arg Glu
             125             130             135

Asn Glu Cys Val Ser Cys Ser Asn Cys Lys Lys Ser Leu Glu Cys Thr
             140             145             150

Lys Leu Cys Leu Pro Gln Ile Glu Asn Val Lys Gly Thr Glu Asp Ser
         155             160             165

Gly Thr Thr Val Leu Leu Pro Leu Val Ile Phe Phe Gly Leu Cys Leu
     170             175             180

Leu Ser Leu Leu Phe Ile Gly Leu Ser Tyr Arg Tyr Gln Arg Trp Lys
185             190             195             200

Ser Lys Leu Tyr Ser Ile Val Cys Gly Lys Ser Thr Pro Glu Lys Glu
             205             210             215

Gly Glu Leu Glu Gly Thr Thr Thr Lys Pro Leu Ala Pro Asn Pro Ser
             220             225             230

Phe Ser Pro Thr Pro Gly Phe Thr Pro Thr Leu Gly Phe Ser Pro Val
         235             240             245

Pro Ser Ser Thr Phe Thr Ser Ser Ser Thr Tyr Thr Pro Gly Asp Cys
 250             255             260

Pro Asn Phe Ala Ala Pro Arg Arg Glu Val Ala Pro Pro Tyr Gln Gly
265             270             275             280

Ala Asp Pro Ile Leu Ala Thr Ala Leu Ala Ser Asp Pro Ile Pro Asn
             285             290             295

Pro Leu Gln Lys Trp Glu Asp Ser Ala His Lys Pro Gln Ser Leu Asp
         300             305             310

Thr Asp Asp Pro Ala Thr Leu Tyr Ala Val Val Glu Asn Val Pro Pro
         315             320             325

Leu Arg Trp Lys Glu Phe Val Arg Arg Leu Gly Leu Ser Asp His Glu
         330             335             340

Ile Asp Arg Leu Glu Leu Gln Asn Gly Arg Cys Leu Arg Glu Ala Gln
345             350             355             360

Tyr Ser Met Leu Ala Thr Trp Arg Arg Arg Thr Pro Arg Arg Glu Ala
             365             370             375

Thr Leu Glu Leu Leu Gly Arg Val Leu Arg Asp Met Asp Leu Leu Gly
             380             385             390

Cys Leu Glu Asp Ile Glu Glu Ala Leu Cys Gly Pro Ala Ala Leu Pro
             395             400             405
```

```
Pro Ala Pro Ser Leu Leu Arg
    410             415

<210> SEQ ID NO 5
<211> LENGTH: 3011
<212> TYPE: DNA
<213> ORGANISM: Homo sapiens
<220> FEATURE:
<221> NAME/KEY: CDS
<222> LOCATION: (84)..(1790)
<223> OTHER INFORMATION:
<220> FEATURE:
<221> NAME/KEY: mat_peptide
<222> LOCATION: (144)..()
<223> OTHER INFORMATION:
<220> FEATURE:
<221> NAME/KEY: sig_peptide
<222> LOCATION: (84)..(143)
<223> OTHER INFORMATION:

<400> SEQUENCE: 5
agacgcaccc tctgaagatg gtggactccc tcctgagaag ctgggacccc ttggtaaaag      60
acaaggcctt ctccaagaag aat atg aaa gtg tta ctc aga ctt att tgt ttc    113
                     Met Lys Val Leu Leu Arg Leu Ile Cys Phe
                         -20                 -15 ata gct cta ctg att tct tct ctg gag gct gat aaa tgc aag gaa cgt      161
Ile Ala Leu Leu Ile Ser Ser Leu Glu Ala Asp Lys Cys Lys Glu Arg
-10                  -5              -1  1               5 gaa gaa aaa ata att tta gtg tca tct gca aat gaa att gat gtt cgt      209
Glu Glu Lys Ile Ile Leu Val Ser Ser Ala Asn Glu Ile Asp Val Arg
            10                  15                  20 ccc tgt cct ctt aac cca aat gaa cac aaa ggc act ata act tgg tat      257
Pro Cys Pro Leu Asn Pro Asn Glu His Lys Gly Thr Ile Thr Trp Tyr
        25                  30                  35 aaa gat gac agc aag aca cct gta tct aca gaa caa gcc tcc agg att      305
Lys Asp Asp Ser Lys Thr Pro Val Ser Thr Glu Gln Ala Ser Arg Ile
    40                  45                  50 cat caa cac aaa gag aaa ctt tgg ttt gtt cct gct aag gtg gag gat      353
His Gln His Lys Glu Lys Leu Trp Phe Val Pro Ala Lys Val Glu Asp
55                  60                  65                  70 tca gga cat tac tat tgc gtg gta aga aat tca tct tac tgc ctc aga      401
Ser Gly His Tyr Tyr Cys Val Val Arg Asn Ser Ser Tyr Cys Leu Arg
                75                  80                  85 att aaa ata agt gca aaa ttt gtg gag aat gag cct aac tta tgt tat      449
Ile Lys Ile Ser Ala Lys Phe Val Glu Asn Glu Pro Asn Leu Cys Tyr
            90                  95                 100 aat gca caa gcc ata ttt aag cag aaa cta ccc gtt gca gga gac gga      497
Asn Ala Gln Ala Ile Phe Lys Gln Lys Leu Pro Val Ala Gly Asp Gly
        105                 110                 115 gga ctt gtg tgc cct tat atg gag ttt ttt aaa aat gaa aat aat gag      545
Gly Leu Val Cys Pro Tyr Met Glu Phe Phe Lys Asn Glu Asn Asn Glu
    120                 125                 130 tta cct aaa tta cag tgg tat aag gat tgc aaa cct cta ctt ctt gac      593
Leu Pro Lys Leu Gln Trp Tyr Lys Asp Cys Lys Pro Leu Leu Leu Asp
135                 140                 145                 150 aat ata cac ttt agt gga gtc aaa gat agg ctc atc gtg atg aat gtg      641
Asn Ile His Phe Ser Gly Val Lys Asp Arg Leu Ile Val Met Asn Val
                155                 160                 165 gct gaa aag cat aga ggg aac tat act tgt cat gca tcc tac aca tac      689
Ala Glu Lys His Arg Gly Asn Tyr Thr Cys His Ala Ser Tyr Thr Tyr
            170                 175                 180 ttg ggc aag caa tat cct att acc cgg gta ata gaa ttt att act cta      737
Leu Gly Lys Gln Tyr Pro Ile Thr Arg Val Ile Glu Phe Ile Thr Leu
```

```
                185                 190                 195
gag gaa aac aaa ccc aca agg cct gtg att gtg agc cca gct aat gag      785
Glu Glu Asn Lys Pro Thr Arg Pro Val Ile Val Ser Pro Ala Asn Glu
        200                 205                 210 aca atg gaa gta gac ttg gga tcc cag ata caa ttg atc tgt aat gtc      833
Thr Met Glu Val Asp Leu Gly Ser Gln Ile Gln Leu Ile Cys Asn Val
215                 220                 225                 230 acc ggc cag ttg agt gac att gct tac tgg aag tgg aat ggg tca gta      881
Thr Gly Gln Leu Ser Asp Ile Ala Tyr Trp Lys Trp Asn Gly Ser Val
                235                 240                 245 att gat gaa gat gac cca gtg cta ggg gaa gac tat tac agt gtg gaa      929
Ile Asp Glu Asp Asp Pro Val Leu Gly Glu Asp Tyr Tyr Ser Val Glu
        250                 255                 260 aat cct gca aac aaa aga agg agt acc ctc atc aca gtg ctt aat ata      977
Asn Pro Ala Asn Lys Arg Arg Ser Thr Leu Ile Thr Val Leu Asn Ile
            265                 270                 275 tcg gaa att gaa agt aga ttt tat aaa cat cca ttt acc tgt ttt gcc     1025
Ser Glu Ile Glu Ser Arg Phe Tyr Lys His Pro Phe Thr Cys Phe Ala
        280                 285                 290 aag aat aca cat ggt ata gat gca gca tat atc cag tta ata tat cca     1073
Lys Asn Thr His Gly Ile Asp Ala Ala Tyr Ile Gln Leu Ile Tyr Pro
295                 300                 305                 310 gtc act aat ttc cag aag cac atg att ggt ata tgt gtc acg ttg aca     1121
Val Thr Asn Phe Gln Lys His Met Ile Gly Ile Cys Val Thr Leu Thr
                315                 320                 325 gtc ata att gtg tgt tct gtt ttc atc tat aaa atc ttc aag att gac     1169
Val Ile Ile Val Cys Ser Val Phe Ile Tyr Lys Ile Phe Lys Ile Asp
        330                 335                 340 att gtg ctt tgg tac agg gat tcc tgc tat gat ttt ctc cca ata aaa     1217
Ile Val Leu Trp Tyr Arg Asp Ser Cys Tyr Asp Phe Leu Pro Ile Lys
            345                 350                 355 gct tca gat gga aag acc tat gac gca tat ata ctg tat cca aag act     1265
Ala Ser Asp Gly Lys Thr Tyr Asp Ala Tyr Ile Leu Tyr Pro Lys Thr
        360                 365                 370 gtt ggg gaa ggg tct acc tct gac tgt gat att ttt gtg ttt aaa gtc     1313
Val Gly Glu Gly Ser Thr Ser Asp Cys Asp Ile Phe Val Phe Lys Val
375                 380                 385                 390 ttg cct gag gtc ttg gaa aaa cag tgt gga tat aag ctg ttc att tat     1361
Leu Pro Glu Val Leu Glu Lys Gln Cys Gly Tyr Lys Leu Phe Ile Tyr
                395                 400                 405 gga agg gat gac tac gtt ggg gaa gac att gtt gag gtc att aat gaa     1409
Gly Arg Asp Asp Tyr Val Gly Glu Asp Ile Val Glu Val Ile Asn Glu
        410                 415                 420 aac gta aag aaa agc aga aga ctg att atc att tta gtc aga gaa aca     1457
Asn Val Lys Lys Ser Arg Arg Leu Ile Ile Ile Leu Val Arg Glu Thr
            425                 430                 435 tca ggc ttc agc tgg ctg ggt ggt tca tct gaa gag caa ata gcc atg     1505
Ser Gly Phe Ser Trp Leu Gly Gly Ser Ser Glu Glu Gln Ile Ala Met
        440                 445                 450 tat aat gct ctt gtt cag gat gga att aaa gtt gtc ctg ctt gag ctg     1553
Tyr Asn Ala Leu Val Gln Asp Gly Ile Lys Val Val Leu Leu Glu Leu
455                 460                 465                 470 gag aaa atc caa gac tat gag aaa atg cca gaa tcg att aaa ttc att     1601
Glu Lys Ile Gln Asp Tyr Glu Lys Met Pro Glu Ser Ile Lys Phe Ile
                475                 480                 485 aag cag aaa cat ggg gct atc cgc tgg tca ggg gac ttt aca cag gga     1649
Lys Gln Lys His Gly Ala Ile Arg Trp Ser Gly Asp Phe Thr Gln Gly
        490                 495                 500 cca cag tct gca aag aca agg ttc tgg aag aat gtc agg tac cac atg     1697
```

```
Pro Gln Ser Ala Lys Thr Arg Phe Trp Lys Asn Val Arg Tyr His Met
        505                 510                 515 cca gtc cag cga cgg tca cct tca tct aaa cac cag tta ctg tca cca    1745
Pro Val Gln Arg Arg Ser Pro Ser Ser Lys His Gln Leu Leu Ser Pro
        520                 525                 530 gcc act aag gag aaa ctg caa aga gag gct cac gtg cct ctc ggg        1790
Ala Thr Lys Glu Lys Leu Gln Arg Glu Ala His Val Pro Leu Gly
535                 540                 545 tagcatggag aagttgccaa gagttcttta ggtgcctcct gtcttatggc gttgcaggcc  1850
aggttatgcc tcatgctgac ttgcagagtt catggaatgt aactatatca tcctttatcc  1910
ctgaggtcac ctggaatcag attattaagg aataagccga tgacgtcaat agcagcccag  1970
ggcacttcag agtagagggc ttgggaagat cttttaaaaa ggcagtaggc ccggtgtggt  2030
ggctcacgcc tataatccca gcactttggg aggctgaagt gggtggatca ccagaggtca  2090
ggagttcgag accagcccag ccaacatggc aaaaccccat ctctactaaa aatacaaaaa  2150
tgagctaggc atggtggcac acgcctgtaa tcccagctac acctgaggct gaggcaggag  2210
aattgcttga accggggaga cggaggttgc agtgagccga gtttgggcca ctgcactcta  2270
gcctggcaac agagcaagac tccgtctcaa aaaagggca ataaatgccc tctctgaatg    2330
tttgaactgc caagaaaagg catggagaca gcgaactaga agaaagggca agaaggaaat  2390
agccaccgtc tacagatggc ttagttaagt catccacagc caagggcgg cggctatgcc    2450
ttgtctgggg accctgtaga gtcactgacc ctggagcggc tctcctgaga ggtgctgcag  2510
gcaaagtgag actgacacct cactgaggaa gggagacata ttcttggaga actttccatc  2570
tgcttgtatt ttccatacac atccccagcc agaagttagt gtccgaagaa gagcttgaaa  2630
actcacttca atgaacaaag ggattctcca ggattccaaa gttttgaagt catcttagct  2690
ttccacagga gggagagaac ttaaaaaagc aacagtagca gggaattgat ccacttctta  2750
atgctttcct ccctggcatg accatcctgt cctttgttat tatcctgcat tttacgtctt  2810
tggaggaaca gctccctagt ggcttcctcc gtctgcaatg tcccttgcac agcccacaca  2870
tgaaccatcc ttcccatgat gccgctcttc tgtcatcccg ctcctgctga aacacctccc  2930
agggctccaa cctgttcagg agctgaagcc catgctttcc caccagcatg tcactcccag  2990
accacctccc tgccctgtcc t                                             3011
```

<210> SEQ ID NO 6
<211> LENGTH: 569
<212> TYPE: PRT
<213> ORGANISM: Homo sapiens

<400> SEQUENCE: 6

```
Met Lys Val Leu Leu Arg Leu Ile Cys Phe Ile Ala Leu Leu Ile Ser
-20                 -15                 -10                  -5

Ser Leu Glu Ala Asp Lys Cys Lys Glu Arg Glu Lys Ile Ile Leu
               -1  1                   5                  10

Val Ser Ala Asn Glu Ile Asp Val Arg Pro Cys Pro Leu Asn Pro
            15                  20                  25

Asn Glu His Lys Gly Thr Ile Thr Trp Tyr Lys Asp Asp Ser Lys Thr
        30                  35                  40

Pro Val Ser Thr Glu Gln Ala Ser Arg Ile His Gln His Lys Glu Lys
45                  50                  55                  60

Leu Trp Phe Val Pro Ala Lys Val Glu Asp Ser Gly His Tyr Tyr Cys
                65                  70                  75
```

-continued

Val Val Arg Asn Ser Ser Tyr Cys Leu Arg Ile Lys Ile Ser Ala Lys
         80                  85                  90

Phe Val Glu Asn Glu Pro Asn Leu Cys Tyr Asn Ala Gln Ala Ile Phe
         95                 100                 105

Lys Gln Lys Leu Pro Val Ala Gly Asp Gly Gly Leu Val Cys Pro Tyr
        110                 115                 120

Met Glu Phe Phe Lys Asn Glu Asn Asn Glu Leu Pro Lys Leu Gln Trp
125                 130                 135                 140

Tyr Lys Asp Cys Lys Pro Leu Leu Leu Asp Asn Ile His Phe Ser Gly
                145                 150                 155

Val Lys Asp Arg Leu Ile Val Met Asn Val Ala Glu Lys His Arg Gly
                160                 165                 170

Asn Tyr Thr Cys His Ala Ser Tyr Thr Tyr Leu Gly Lys Gln Tyr Pro
        175                 180                 185

Ile Thr Arg Val Ile Glu Phe Ile Thr Leu Glu Glu Asn Lys Pro Thr
        190                 195                 200

Arg Pro Val Ile Val Ser Pro Ala Asn Glu Thr Met Glu Val Asp Leu
205                 210                 215                 220

Gly Ser Gln Ile Gln Leu Ile Cys Asn Val Thr Gly Gln Leu Ser Asp
                225                 230                 235

Ile Ala Tyr Trp Lys Trp Asn Gly Ser Val Ile Asp Glu Asp Asp Pro
                240                 245                 250

Val Leu Gly Glu Asp Tyr Tyr Ser Val Glu Asn Pro Ala Asn Lys Arg
                255                 260                 265

Arg Ser Thr Leu Ile Thr Val Leu Asn Ile Ser Glu Ile Glu Ser Arg
                270                 275                 280

Phe Tyr Lys His Pro Phe Thr Cys Phe Ala Lys Asn Thr His Gly Ile
285                 290                 295                 300

Asp Ala Ala Tyr Ile Gln Leu Ile Tyr Pro Val Thr Asn Phe Gln Lys
                305                 310                 315

His Met Ile Gly Ile Cys Val Thr Leu Thr Val Ile Ile Val Cys Ser
                320                 325                 330

Val Phe Ile Tyr Lys Ile Phe Lys Ile Asp Ile Val Leu Trp Tyr Arg
                335                 340                 345

Asp Ser Cys Tyr Asp Phe Leu Pro Ile Lys Ala Ser Asp Gly Lys Thr
                350                 355                 360

Tyr Asp Ala Tyr Ile Leu Tyr Pro Lys Thr Val Gly Glu Gly Ser Thr
365                 370                 375                 380

Ser Asp Cys Asp Ile Phe Val Phe Lys Val Leu Pro Glu Val Leu Glu
                385                 390                 395

Lys Gln Cys Gly Tyr Lys Leu Phe Ile Tyr Gly Arg Asp Asp Tyr Val
                400                 405                 410

Gly Glu Asp Ile Val Glu Val Ile Asn Glu Asn Val Lys Lys Ser Arg
                415                 420                 425

Arg Leu Ile Ile Ile Leu Val Arg Glu Thr Ser Gly Phe Ser Trp Leu
        430                 435                 440

Gly Gly Ser Ser Glu Glu Gln Ile Ala Met Tyr Asn Ala Leu Val Gln
445                 450                 455                 460

Asp Gly Ile Lys Val Val Leu Leu Glu Leu Glu Lys Ile Gln Asp Tyr
                465                 470                 475

Glu Lys Met Pro Glu Ser Ile Lys Phe Ile Lys Gln Lys His Gly Ala
                480                 485                 490

Ile Arg Trp Ser Gly Asp Phe Thr Gln Gly Pro Gln Ser Ala Lys Thr

-continued

```
              495                 500                 505
Arg Phe Trp Lys Asn Val Arg Tyr His Met Pro Val Gln Arg Arg Ser
        510                 515                 520
Pro Ser Ser Lys His Gln Leu Leu Ser Pro Ala Thr Lys Glu Lys Leu
525                 530                 535                 540
Gln Arg Glu Ala His Val Pro Leu Gly
                545

<210> SEQ ID NO 7
<211> LENGTH: 1357
<212> TYPE: DNA
<213> ORGANISM: Homo sapiens
<220> FEATURE:
<221> NAME/KEY: CDS
<222> LOCATION: (154)..(1347)
<223> OTHER INFORMATION:
<220> FEATURE:
<221> NAME/KEY: mat_peptide
<222> LOCATION: (193)..()
<223> OTHER INFORMATION:
<220> FEATURE:
<221> NAME/KEY: sig_peptide
<222> LOCATION: (154)..(192)
<223> OTHER INFORMATION:

<400> SEQUENCE: 7
ctggaaaata cattctgcta ctcttaaaaa ctagtgacgc tcatacaaat caacagaaag      60
agcttctgaa ggaagacttt aaagctgctt ctgccacgtg ctgctgggtc tcagtcctcc    120
acttcccgtg tcctctggaa gttgtcagga gca atg ttg cgc ttg tac gtg ttg    174
                                    Met Leu Arg Leu Tyr Val Leu
                                                        -10 gta atg gga gtt tct gcc ttc acc ctt cag cct gcg gca cac aca ggg    222
Val Met Gly Val Ser Ala Phe Thr Leu Gln Pro Ala Ala His Thr Gly
 -5              -1   1               5                    10 gct gcc aga agc tgc cgg ttt cgt ggg agg cat tac aag cgg gag ttc    270
Ala Ala Arg Ser Cys Arg Phe Arg Gly Arg His Tyr Lys Arg Glu Phe
                15                  20                  25 agg ctg gaa ggg gag cct gta gcc ctg agg tgc ccc cag gtg ccc tac    318
Arg Leu Glu Gly Glu Pro Val Ala Leu Arg Cys Pro Gln Val Pro Tyr
            30                  35                  40 tgg ttg tgg gcc tct gtc agc ccc cgc atc aac ctg aca tgg cat aaa    366
Trp Leu Trp Ala Ser Val Ser Pro Arg Ile Asn Leu Thr Trp His Lys
        45                  50                  55 aat gac tct gct agg acg gtc cca gga gaa gaa gag aca ggg atg tgg    414
Asn Asp Ser Ala Arg Thr Val Pro Gly Glu Glu Glu Thr Gly Met Trp
    60                  65                  70 gcc cag gac ggt gct ctg tgg ctt ctg cca gcc ttg cag gag gac tct    462
Ala Gln Asp Gly Ala Leu Trp Leu Leu Pro Ala Leu Gln Glu Asp Ser
75                  80                  85                  90 ggc acc tac gtc tgc act act aga aat gct tct tac tgt gac aaa atg    510
Gly Thr Tyr Val Cys Thr Thr Arg Asn Ala Ser Tyr Cys Asp Lys Met
                95                  100                 105 tcc att gag ctc aga gtt ttt gag aat aca gat gct ttc ctg ccg ttc    558
Ser Ile Glu Leu Arg Val Phe Glu Asn Thr Asp Ala Phe Leu Pro Phe
            110                 115                 120 atc tca tac ccg caa att tta acc ttg tca acc tct ggg gta tta gta    606
Ile Ser Tyr Pro Gln Ile Leu Thr Leu Ser Thr Ser Gly Val Leu Val
        125                 130                 135 tgc cct gac ctg agt gaa ttc acc cgt gac aaa act gac gtg aag att    654
Cys Pro Asp Leu Ser Glu Phe Thr Arg Asp Lys Thr Asp Val Lys Ile
    140                 145                 150
```

```
caa tgg tac aag gat tct ctt ctt ttg gat aaa gac aat gag aaa ttt        702
Gln Trp Tyr Lys Asp Ser Leu Leu Leu Asp Lys Asp Asn Glu Lys Phe
155                 160                 165                 170 cta agt gtg agg ggg acc act cac tta ctc gta cac gat gtg gcc ctg        750
Leu Ser Val Arg Gly Thr Thr His Leu Leu Val His Asp Val Ala Leu
            175                 180                 185 gaa gat gct ggc tat tac cgc tgt gtc ctg aca ttt gcc cat gaa ggc        798
Glu Asp Ala Gly Tyr Tyr Arg Cys Val Leu Thr Phe Ala His Glu Gly
        190                 195                 200 cag caa tac aac atc act agg agt att gag cta cgc atc aag aaa aaa        846
Gln Gln Tyr Asn Ile Thr Arg Ser Ile Glu Leu Arg Ile Lys Lys Lys
    205                 210                 215 aaa gaa gag acc att cct gtg atc att tcc ccc ctc aag acc ata tca        894
Lys Glu Glu Thr Ile Pro Val Ile Ile Ser Pro Leu Lys Thr Ile Ser
220                 225                 230 gct tct ctg ggg tca aga ctg aca atc ccg tgt aag gtg ttt ctg gga        942
Ala Ser Leu Gly Ser Arg Leu Thr Ile Pro Cys Lys Val Phe Leu Gly
235                 240                 245                 250 acc ggc aca ccc tta acc acc atg ctg tgg tgg acg gcc aat gac acc        990
Thr Gly Thr Pro Leu Thr Thr Met Leu Trp Trp Thr Ala Asn Asp Thr
            255                 260                 265 cac ata gag agc gcc tac ccg gga ggc cgc gtg acc gag ggg cca cgc       1038
His Ile Glu Ser Ala Tyr Pro Gly Gly Arg Val Thr Glu Gly Pro Arg
        270                 275                 280 cag gaa tat tca gaa aat aat gag aac tac att gaa gtg cca ttg att       1086
Gln Glu Tyr Ser Glu Asn Asn Glu Asn Tyr Ile Glu Val Pro Leu Ile
    285                 290                 295 ttt gat cct gtc aca aga gag gat ttg cac atg gat ttt aaa tgt gtt       1134
Phe Asp Pro Val Thr Arg Glu Asp Leu His Met Asp Phe Lys Cys Val
300                 305                 310 gtc cat aat acc ctg agt ttt cag aca cta cgc acc aca gtc aag gaa       1182
Val His Asn Thr Leu Ser Phe Gln Thr Leu Arg Thr Thr Val Lys Glu
315                 320                 325                 330 gcc tcc tcc acg ttc tcc tgg ggc att gtg ctg gcc cca ctt tca ctg       1230
Ala Ser Ser Thr Phe Ser Trp Gly Ile Val Leu Ala Pro Leu Ser Leu
            335                 340                 345 gcc ttc ttg gtt ttg ggg gga ata tgg atg cac aga cgg tgc aaa cac       1278
Ala Phe Leu Val Leu Gly Gly Ile Trp Met His Arg Arg Cys Lys His
        350                 355                 360 aga act gga aaa gca gat ggt ctg act gtg cta tgg cct cat cat caa       1326
Arg Thr Gly Lys Ala Asp Gly Leu Thr Val Leu Trp Pro His His Gln
    365                 370                 375 gac ttt caa tcc tat ccc aag tgaaataaat                                 1357
Asp Phe Gln Ser Tyr Pro Lys
380                 385

<210> SEQ ID NO 8
<211> LENGTH: 398
<212> TYPE: PRT
<213> ORGANISM: Homo sapiens

<400> SEQUENCE: 8

Met Leu Arg Leu Tyr Val Leu Val Met Gly Val Ser Ala Phe Thr Leu
            -10                 -5                  -1   1

Gln Pro Ala Ala His Thr Gly Ala Ala Arg Ser Cys Arg Phe Arg Gly
            5                   10                  15

Arg His Tyr Lys Arg Glu Phe Arg Leu Glu Gly Glu Pro Val Ala Leu
20                  25                  30                  35

Arg Cys Pro Gln Val Pro Tyr Trp Leu Trp Ala Ser Val Ser Pro Arg
            40                  45                  50
```

Ile Asn Leu Thr Trp His Lys Asn Asp Ser Ala Arg Thr Val Pro Gly
            55                  60                  65

Glu Glu Glu Thr Gly Met Trp Ala Gln Asp Gly Ala Leu Trp Leu Leu
        70                  75                  80

Pro Ala Leu Gln Glu Asp Ser Gly Thr Tyr Val Cys Thr Thr Arg Asn
    85                  90                  95

Ala Ser Tyr Cys Asp Lys Met Ser Ile Glu Leu Arg Val Phe Glu Asn
100                 105                 110                 115

Thr Asp Ala Phe Leu Pro Phe Ile Ser Tyr Pro Gln Ile Leu Thr Leu
                120                 125                 130

Ser Thr Ser Gly Val Leu Val Cys Pro Asp Leu Ser Glu Phe Thr Arg
            135                 140                 145

Asp Lys Thr Asp Val Lys Ile Gln Trp Tyr Lys Asp Ser Leu Leu Leu
            150                 155                 160

Asp Lys Asp Asn Glu Lys Phe Leu Ser Val Arg Gly Thr Thr His Leu
        165                 170                 175

Leu Val His Asp Val Ala Leu Glu Asp Ala Gly Tyr Tyr Arg Cys Val
180                 185                 190                 195

Leu Thr Phe Ala His Glu Gly Gln Gln Tyr Asn Ile Thr Arg Ser Ile
                200                 205                 210

Glu Leu Arg Ile Lys Lys Lys Glu Thr Ile Pro Val Ile Ile
            215                 220                 225

Ser Pro Leu Lys Thr Ile Ser Ala Ser Leu Gly Ser Arg Leu Thr Ile
            230                 235                 240

Pro Cys Lys Val Phe Leu Gly Thr Gly Thr Pro Leu Thr Thr Met Leu
        245                 250                 255

Trp Trp Thr Ala Asn Asp Thr His Ile Glu Ser Ala Tyr Pro Gly Gly
260                 265                 270                 275

Arg Val Thr Glu Gly Pro Arg Gln Glu Tyr Ser Glu Asn Asn Glu Asn
                280                 285                 290

Tyr Ile Glu Val Pro Leu Ile Phe Asp Pro Val Thr Arg Glu Asp Leu
            295                 300                 305

His Met Asp Phe Lys Cys Val Val His Asn Thr Leu Ser Phe Gln Thr
        310                 315                 320

Leu Arg Thr Thr Val Lys Glu Ala Ser Ser Thr Phe Ser Trp Gly Ile
    325                 330                 335

Val Leu Ala Pro Leu Ser Leu Ala Phe Leu Val Leu Gly Gly Ile Trp
340                 345                 350                 355

Met His Arg Arg Cys Lys His Arg Thr Gly Lys Ala Asp Gly Leu Thr
                360                 365                 370

Val Leu Trp Pro His His Gln Asp Phe Gln Ser Tyr Pro Lys
            375                 380                 385

<210> SEQ ID NO 9
<211> LENGTH: 30
<212> TYPE: DNA
<213> ORGANISM: Artificial Sequence
<220> FEATURE:
<223> OTHER INFORMATION: Miscellaneous Structure

<400> SEQUENCE: 9
ctgaagggag cactggcgac taaggatcca                                30

<210> SEQ ID NO 10
<211> LENGTH: 45

```
<212> TYPE: DNA
<213> ORGANISM: Artificial Sequence
<220> FEATURE:
<223> OTHER INFORMATION: Miscellaneous Structure

<400> SEQUENCE: 10
gatctgtaac gtggtggcca tccctgggaa tgcaagcatg gatgc            45

<210> SEQ ID NO 11
<211> LENGTH: 33
<212> TYPE: DNA
<213> ORGANISM: Artificial Sequence
<220> FEATURE:
<223> OTHER INFORMATION: Miscellaneous Structure

<400> SEQUENCE: 11
agtctgcacg tccacgtccc ccaccggtg agc                          33

<210> SEQ ID NO 12
<211> LENGTH: 12
<212> TYPE: DNA
<213> ORGANISM: Artificial Sequence
<220> FEATURE:
<223> OTHER INFORMATION: Miscellaneous Structure

<400> SEQUENCE: 12
gatctgttga gc                                                12

<210> SEQ ID NO 13
<211> LENGTH: 36
<212> TYPE: DNA
<213> ORGANISM: Artificial Sequence
<220> FEATURE:
<223> OTHER INFORMATION: Miscellaneous Structure

<400> SEQUENCE: 13
ctgaaacatc agacgtggtg tgcaagccct gttaaa                      36

<210> SEQ ID NO 14
<211> LENGTH: 29
<212> TYPE: DNA
<213> ORGANISM: Artificial Sequence
<220> FEATURE:
<223> OTHER INFORMATION: Miscellaneous Structure

<400> SEQUENCE: 14
gcgtcgacct agtgacgctc atacaaatc                              29

<210> SEQ ID NO 15
<211> LENGTH: 33
<212> TYPE: DNA
<213> ORGANISM: Artificial Sequence
<220> FEATURE:
<223> OTHER INFORMATION: Miscellaneous Structure

<400> SEQUENCE: 15
gcgcggccgc tcaggaggag gcttccttga ctg                         33

<210> SEQ ID NO 16
<211> LENGTH: 66
<212> TYPE: DNA
<213> ORGANISM: Artificial Sequence
<220> FEATURE:
<223> OTHER INFORMATION: Miscellaneous Structure
<220> FEATURE:
<221> NAME/KEY: CDS
<222> LOCATION: (3)..(65)
```

<223> OTHER INFORMATION:

<400> SEQUENCE: 16

```
ct gaa ggg agc act ggc gac ggt ggc ggt gga tcc ggt ggc ggc        47
   Glu Gly Ser Thr Gly Asp Gly Gly Gly Ser Gly Gly Gly
   1               5                  10                 15 ggc tca ttg ccc gcc cag g                                         66
Gly Ser Leu Pro Ala Gln
            20
```

<210> SEQ ID NO 17
<211> LENGTH: 21
<212> TYPE: PRT
<213> ORGANISM: Artificial Sequence
<220> FEATURE:
<223> OTHER INFORMATION: Miscellaneous Structure

<400> SEQUENCE: 17

```
Glu Gly Ser Thr Gly Asp Gly Gly Gly Ser Gly Gly Gly Gly
1               5                  10                  15

Ser Leu Pro Ala Gln
            20
```

<210> SEQ ID NO 18
<211> LENGTH: 17
<212> TYPE: DNA
<213> ORGANISM: Artificial Sequence
<220> FEATURE:
<223> OTHER INFORMATION: Miscellaneous Structure

<400> SEQUENCE: 18
accgagggac ctgagcg                                                17

<210> SEQ ID NO 19
<211> LENGTH: 53
<212> TYPE: DNA
<213> ORGANISM: Artificial Sequence
<220> FEATURE:
<223> OTHER INFORMATION: Miscellaneous Structure

<400> SEQUENCE: 19
tgagccgccg ccaccgccgg atccaccgcc accagtgact ggatatatta act        53

<210> SEQ ID NO 20
<211> LENGTH: 51
<212> TYPE: DNA
<213> ORGANISM: Artificial Sequence
<220> FEATURE:
<223> OTHER INFORMATION: Miscellaneous Structure

<400> SEQUENCE: 20
ggtggcggtg gatccggcgg tggcggcggc tcattgcccg cccaggtggc a           51

<210> SEQ ID NO 21
<211> LENGTH: 18
<212> TYPE: DNA
<213> ORGANISM: Artificial Sequence
<220> FEATURE:
<223> OTHER INFORMATION: Miscellaneous Structure

<400> SEQUENCE: 21
gcttgctcag cgcgcagt                                               18

<210> SEQ ID NO 22
<211> LENGTH: 5

```
<212> TYPE: PRT
<213> ORGANISM: Artificial Sequence
<220> FEATURE:
<223> OTHER INFORMATION: Miscellaneous Structure

<400> SEQUENCE: 22

Gly Gly Gly Gly Ser
1               5

<210> SEQ ID NO 23
<211> LENGTH: 11
<212> TYPE: PRT
<213> ORGANISM: Artificial Sequence
<220> FEATURE:
<223> OTHER INFORMATION: Miscellaneous Structure

<400> SEQUENCE: 23

Gly Gly Gly Gly Ser Gly Gly Gly Gly Ser
1               5                   10

<210> SEQ ID NO 24
<211> LENGTH: 22
<212> TYPE: PRT
<213> ORGANISM: Artificial Sequence
<220> FEATURE:
<223> OTHER INFORMATION: Miscellaneous Structure

<400> SEQUENCE: 24

Gly Gly Gly Gly Ser Gly Gly Gly Gly Ser Gly Gly Gly Gly Ser
1               5                   10                  15

Gly Gly Gly Gly Gly Ser
            20

<210> SEQ ID NO 25
<211> LENGTH: 6
<212> TYPE: PRT
<213> ORGANISM: Artificial Sequence
<220> FEATURE:
<223> OTHER INFORMATION: Miscellaneous Structure

<400> SEQUENCE: 25

Asp Ser Val Cys Pro Gln
1               5

<210> SEQ ID NO 26
<211> LENGTH: 6
<212> TYPE: PRT
<213> ORGANISM: Artificial Sequence
<220> FEATURE:
<223> OTHER INFORMATION: Miscellaneous Structure

<400> SEQUENCE: 26

Leu Pro Ala Gln Val Ala
1               5

<210> SEQ ID NO 27
<211> LENGTH: 5
<212> TYPE: PRT
<213> ORGANISM: Artificial Sequence
<220> FEATURE:
<223> OTHER INFORMATION: Miscellaneous Structure

<400> SEQUENCE: 27

Val Ala Phe Thr Pro
1               5
```

```
<210> SEQ ID NO 28
<211> LENGTH: 8
<212> TYPE: PRT
<213> ORGANISM: Artificial Sequence
<220> FEATURE:
<223> OTHER INFORMATION: Miscellaneous Structure

<400> SEQUENCE: 28

Asp Tyr Lys Asp Asp Asp Asp Lys
1               5

<210> SEQ ID NO 29
<211> LENGTH: 10
<212> TYPE: PRT
<213> ORGANISM: Artificial Sequence
<220> FEATURE:
<223> OTHER INFORMATION: Miscellaneous Structure

<400> SEQUENCE: 29

Gly Gly Gly Gly Ser Gly Gly Gly Gly Ser
1               5                   10
```